(12) United States Patent
DiMilla et al.

(10) Patent No.: US 7,348,176 B2
(45) Date of Patent: *Mar. 25, 2008

(54) CHAMBER WITH ADJUSTABLE VOLUME FOR CELL CULTURE AND ORGAN ASSIST

(75) Inventors: Paul A. DiMilla, Dover, MA (US); Maury D. Cosman, Medfield, MA (US); Rachel Halych, Quincy, MA (US); Lisa Romito, Brookline, MA (US); Chris Gemmeti, Atlanta, GA (US); Kevin Odlum, Springfield, MA (US)

(73) Assignee: Organogenesis, Inc., Canton, MA (US)

( * ) Notice: Subject to any disclaimer, the term of this patent is extended or adjusted under 35 U.S.C. 154(b) by 292 days.

This patent is subject to a terminal disclaimer.

(21) Appl. No.: 11/057,772

(22) Filed: Feb. 14, 2005

(65) Prior Publication Data

US 2006/0003436 A1  Jan. 5, 2006

Related U.S. Application Data

(63) Continuation of application No. 10/325,437, filed on Dec. 19, 2002, now Pat. No. 6,855,542.

(60) Provisional application No. 60/342,992, filed on Dec. 21, 2001.

(51) Int. Cl.
*C12M 3/00* (2006.01)

(52) U.S. Cl. .............................. 435/289.1; 435/304.3; 435/383; 424/94.7

(58) Field of Classification Search ..................... None
See application file for complete search history.

(56) References Cited

U.S. PATENT DOCUMENTS 6,855,542 B2 *  2/2005  DiMilla et al. .......... 435/289.1

* cited by examiner

*Primary Examiner*—James Ketter
(74) *Attorney, Agent, or Firm*—Edward J. Adamson

(57) ABSTRACT

The invention features modular chambers for culturing cells in which the volume of a chamber can be adjusted without compromising the seal or sterility of the chamber. The invention is based on the principle that the volume of a chamber formed between two plates sandwiching a compressible gasket and a substantially incompressible stop can be adjusted using a gasket that forms a fluid-tight seal between the plates at a plurality of levels of compression. The invention enables the culture of cells between substantially parallel and rigid plates in which a relatively large volume can be used to seed the cells and the holdup volume reduced for perfusion without opening or otherwise disassembling the system to compromise its liquidtightness and sterility. The new closed, modular and scalable cell-culturing chamber can be thus perfused and used to culture cells (e.g., hepatocytes) with high levels of cell function in organ (e.g., liver) assist systems, for production of cells, for production of cell-derived products, such as proteins or viruses, or for systems to treat biological liquids to remove toxins, such as ammonia, add cell-synthesized products, or both.

9 Claims, 17 Drawing Sheets

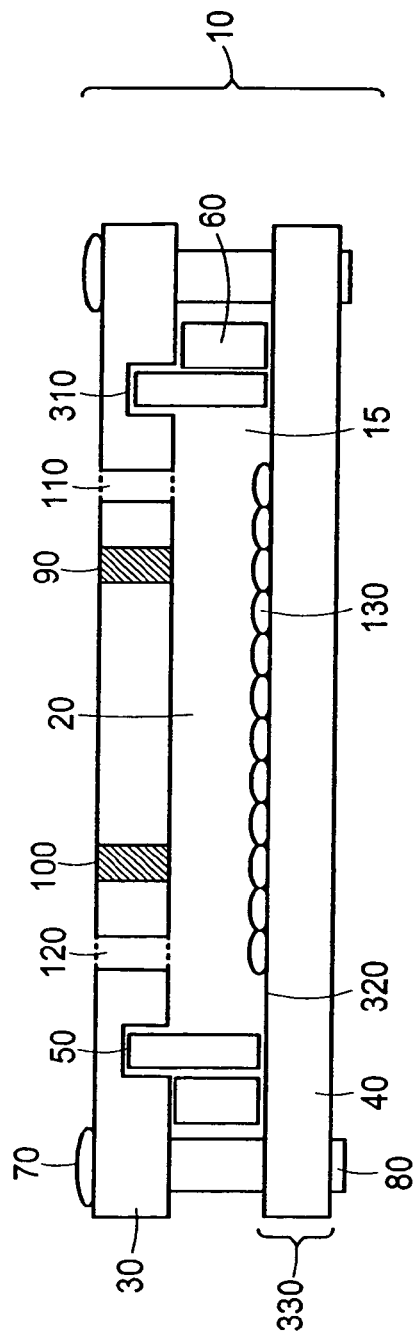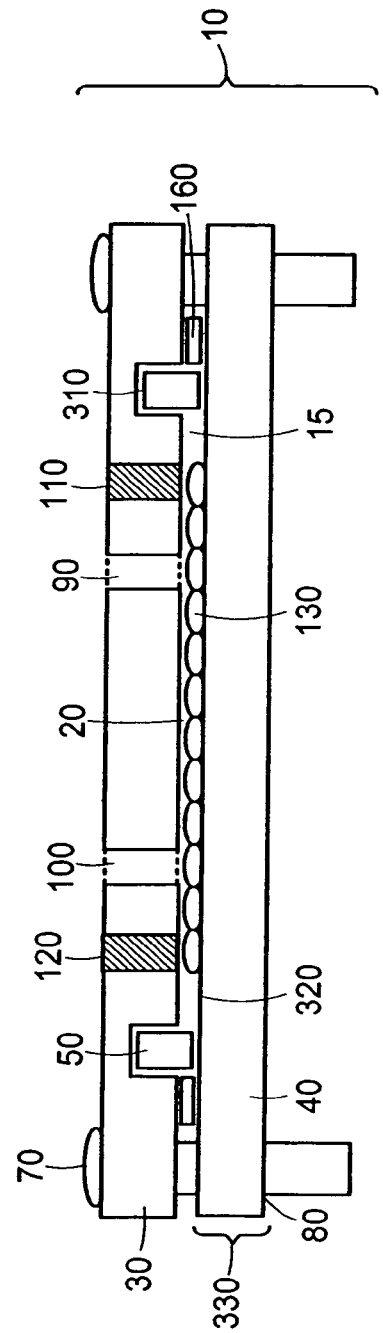

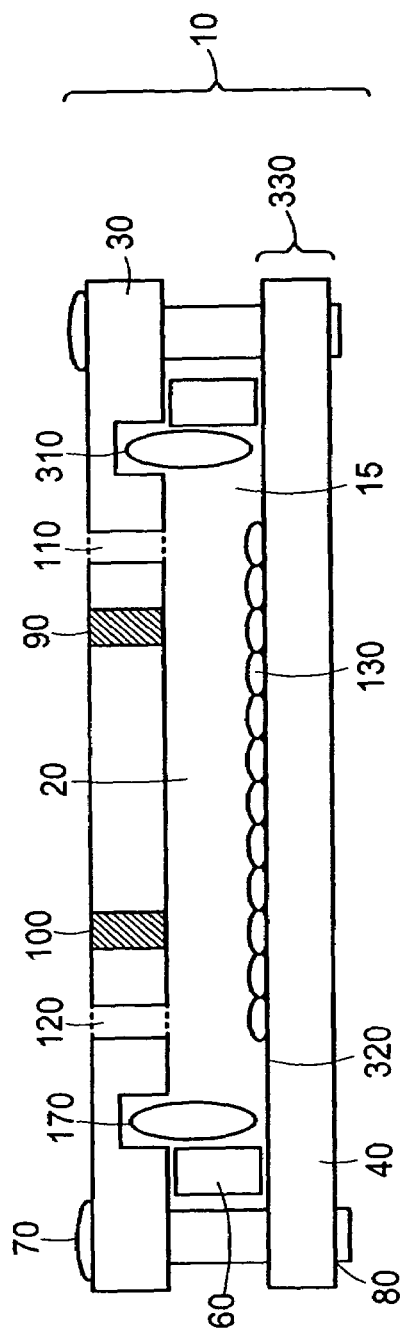
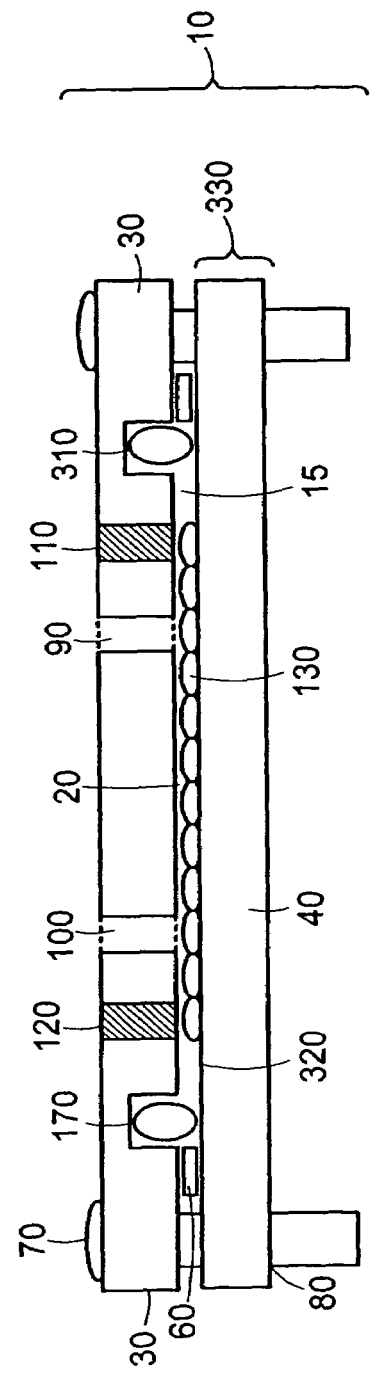
FIG. 3A
FIG. 3B

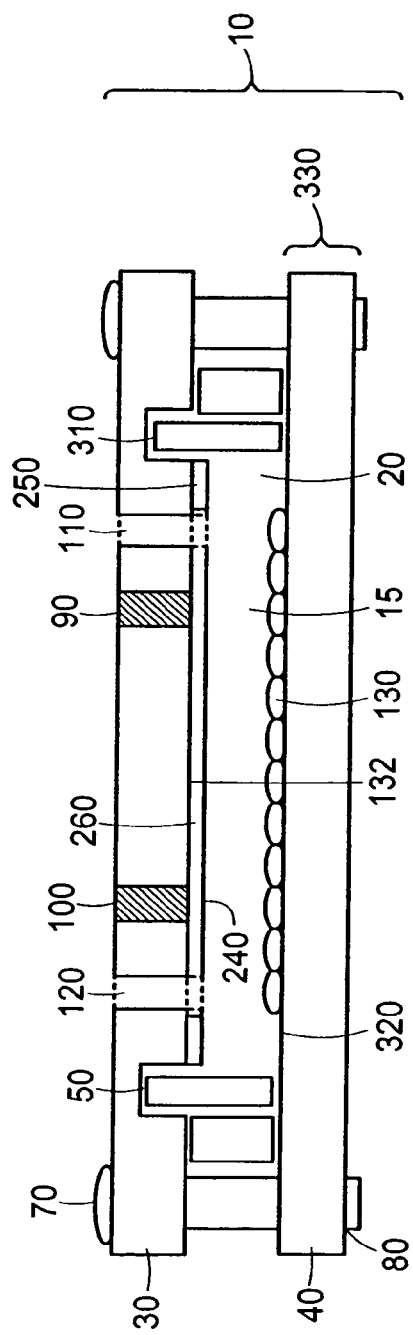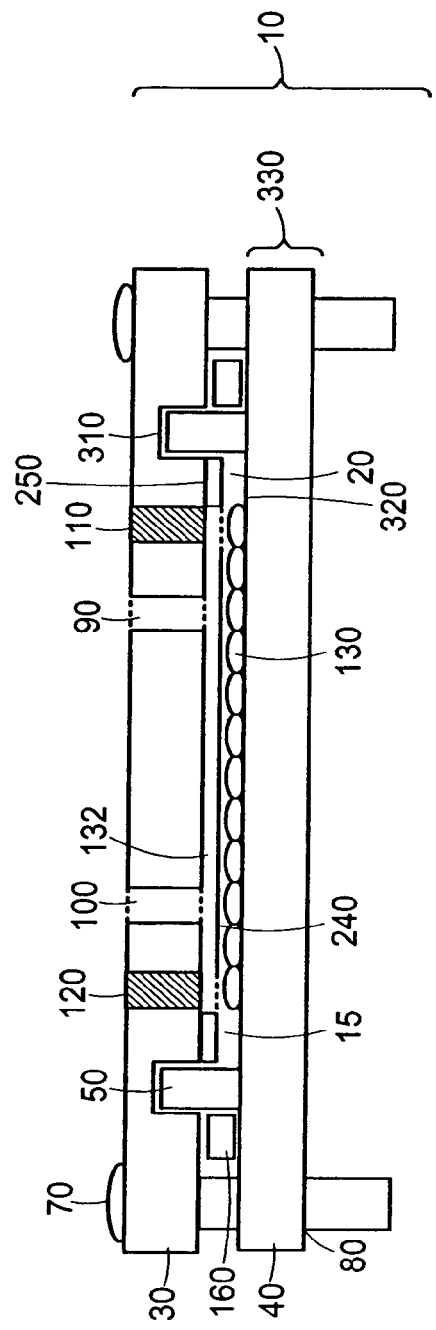

CHAMBER WITH ADJUSTABLE VOLUME FOR CELL CULTURE AND ORGAN ASSIST

CROSS-REFERENCE TO RELATED APPLICATION

This application is a Continuation of U.S. patent application Ser. No. 10/325,437 which was filed on Dec. 19, 2002 and which claims the benefit of U.S. Provisional Application Ser. No. 60/342,992 entitled "CHAMBER WITH ADJUSTABLE VOLUME FOR CELL CULTURE AND ORGAN ASSIST" filed on Dec. 21, 2001, which are incorporated herein by reference in their entirety.

FIELD OF THE INVENTION

The invention relates to systems and methods of culturing cells in chambers for cell culture and tissue engineering and for organ assist devices.

BACKGROUND OF THE INVENTION

Devices, chambers, and apparati for culturing cells are a major focus in the biotechnology industry as systems for producing cells and cell-derived compounds as well as for using cells in tissue-engineering products as systems for therapeutic treatment and gene therapy. Although a wide variety of devices for cell culture have been conceived, developed, and applied in the last century, the need for novel and improved systems remains, in part because of unresolved limitations with existing devices and in part because of new applications with requirements not anticipated by existing devices. Unresolved limitations with current devices for cell culture include: (1) the inability to seed and distribute cells in devices at the relatively high ratios of volume of medium to cell number necessary for supporting cell inoculation (e.g., adhesion and spreading for attachment dependent cells) while reducing the volume per cell for advantageous cell function, growth, and concentration of cell-derived products, (2) inherent deficiencies in scaling of performance of cell cultures with increases in size of devices, and (3) incapabilities with economically-feasible scales of manufacturing that insure compliance with regulatory concerns. These problems are compounded by requirements for decreased limitations in mass transfer, the need to minimize holdup volume of perfused devices to limit hemodilution during in vivo treatment using cell cultures, and maximizing function of finicky cell cultures (e.g., stem cells that rapidly differentiate into undesired lineages).

Consideration of existing devices for cell culture and, in particular, for devices suitable for culture of fragile adhesion-dependent mammalian cells, illustrates the limitations and deficiencies that warrant addressing. For example, almost every device for cell culture previously disclosed lacks the ability to control the volume contained within the chamber housing the cells without changing the component comprising the walls of the chamber itself and/or compromising the sterility of the chamber and supported cell culture. The two types of devices providing for variable volume during cell culture without compromising sterility of the culture that have been described, moreover, present significant restrictions that hinder their application. Several forms of a chamber for cell culture based on a bag, which conceptually could allow variable volumes for cultures, have been described previously (e.g., U.S. Pat. Nos. 5,686,304 and 5,714,384), but the flexible walls present in these and other bags do not provide tight control of volumes, do not provide rigid surfaces for culture of adherent cells, nor present chambers with well-defined geometries for well-defined perfusions (e.g., uniform hydrodynamic shear stresses required for many adherent cells). Deformability of a wall of a chamber in general (e.g., as practiced by U.S. Pat. No. 6,152,163), leads to these inherent limitations. Alternatively, U.S. Pat. No. 5,707,868 describes the use of a piston-based design as a variable-volume chamber for cell culture. This type of design, similar in concept to other piston-based designs for biotechnological applications described in U.S. Pat. Nos. 5,143,847, 6,007,472, and 6,290,910, are cumbersome mechanically and not well-suited to large, planar cultures of adherent monolayers.

A review of previous designs of devices for cell culture supports the need for creation of an apparatus for the scalable culture of cells between substantially parallel, rigid flat plates in which a relatively large volume can be used to seed the cells and the holdup volume within the chamber itself reduced for perfusion without opening or otherwise disassembling the system to compromise its liquid-tightness and sterility. Such a device also should not require extensive handling or disassembly of the device between seeding and subsequent perfusion, such as by removal of a seeding well, and should improve on the normally labor-intensive process of cell culture while facilitating aseptic processing. A fully closed system in which cells are pumped directly into a chamber without direct exposure to the outside atmosphere, allowed to settle and attach, seeding medium removed, and perfusion of defined medium or plasma established with minimal disassembly or exposure would be compatible with these requirements. Further, these desired characteristics are even more critical for larger devices because the risk of contamination increases with size of device and reliable loading of cells becomes more difficult.

The development and application of devices allowing the culture of cells at high densities is of special importance to extracorporeal treatments for patients with diseased or otherwise failing organs. Such devices have applicability as therapies for other patients with islet failure (e.g., in diabetes), kidney failure, failure of endocrine organs (e.g., the adrenal glands), and impaired hematopoiesis (e.g., in cancer of the bone marrow).

The application of new forms of cell culture devices for treatment of individuals suffering from impaired liver function is a particularly pressing need. Over 43,000 Americans die each year from liver disease, making it the tenth leading disease-related cause of death in the US. When liver disease progresses to liver failure, the mortality is 80% unless a compatible donor organ is found. As with other organs, there is a critical shortage of donor livers. Over 12,000 patients currently are listed as transplant candidates, but fewer than half that number of donor livers become available each year. Treatment with a liver assist device (LAD) would decrease the mortality associated with liver failure by stabilizing patients so that they are suitable candidates for a transplant, by supporting them until a suitable donor liver becomes available, and/or by preventing deterioration to the point where a liver transplant is required. Improving the pre-operative health of these patients would also increase transplant success, thereby decreasing the frequency of retransplantation and easing the demand for donor organs.

In cases of sudden or hepatic failure, which often occur as a result of viral infection or toxicity, treatment with a LAD would eliminate the need for a transplant by supporting these individuals until their own livers regenerate. Liver transplantation is currently the most expensive organ transplant procedure. Successful development of a LAD would consequently provide major benefits to the US in reduced deaths and health-care costs.

Extracorporeal devices for temporary liver support have been investigated since the 1960s. Two strategies have been explored in the development of liver assist devices: (1) non-biological devices based on hemoperfusion on sorbents, hemodialysis across selectively-permeable membranes, and plasma exchange (Malchesky, "Non-biological liver support: historic overview," *Artif. Organs* 18: 342-347, 1994); and (2) biological devices that incorporate cells or cellular components (Yarmush et al., "Assessment of artificial liver support technology," *Cell Trans.* 1: 323-341, 1992).

Non-biological devices have shown only limited efficacy, confirming that synthetic materials cannot replace the range and level of complex metabolic functions normally performed by the liver. On the other hand, a biological LAD in which hepatocytes are seeded on the outer surface of hollow fibers and blood or plasma circulates through the lumen of these fibers was proposed almost 25 years ago by Wolf and colleagues (Wolf et al., "Bilirubin conjugation by an artificial liver composed of cultured cells and synthetic capillaries," *Trans. Amer. Soc. Artif Int. Organs* 21: 16-23, 1975). It is desirable in such a LAD to provide the range of functions provided by hepatocytes in healthy livers, including clearance of protein catabolic products (e.g., hemoglobin from the turnover of red blood cells), detoxification of xenobiotics (compounds foreign to an organism), gluconeogenesis, homeostasis for lipids, minerals, vitamins, and cofactors, and regulation of blood composition (e.g., by secretion of carrier proteins like albumin and clotting factors).

Current designs for a biological LAD use the inverse of this concept today. Modern designs are often based on providing critical liver function by supporting high-density hepatocyte suspensions in hollow fibers, with circulation of blood or plasma outside the fibers. In this design, intermittent extracorporeal liver function is to be provided until the patient recovers through liver regeneration or until a transplant becomes available. However, the design based on hollow fibers is limited by several factors, including: a) inadequate mass transport, b) lack of scalability for sizing, c) lack of modularity for flexibility in design and assembly, d) poor control over distribution of cells, particularly during loading, e) inadequate support of hepatocytes during seeding, including limitations in volume of supporting medium, f) incompatibility with aseptic processing, g) constraints for void volume on the perfusion circuit for the device, and h) dynamics in mixing between device contents and patients' plasma due to constraints in the design of interface between device and patient. For example, it is desirable to perfuse ex vivo relatively large numbers of cells, up to 10% or more of the approximately $2\text{-}5\times10^{11}$ hepatocytes in a healthy adult, at high densities (to minimize dilutional effects on plasma during treatment) and with significant differentiated function.

Hollow fibers have been chosen for LADs on the basis of ready availability rather than demonstrated ability to support hepatocyte function. Perfusion of high-density hepatocyte cultures in hollow fibers has shown a lack of convincing benefit due to, among other reasons, transport limitations that undermine their support of high-density cultures. Such limitations are particularly acute for oxygen, which is required for both basic metabolic function as well as for initial steps in detoxification. Perfusion of oxygenated plasma or medium through or around a network of hollow fibers fails to address this problem because these aqueous liquids are poor carriers for oxygen and the associated distances for transport are relatively large. Modifications to the core hollow-fiber design (e.g., the use of a woven network of three independent sets of capillaries providing integral oxygenation as disclosed in U.S. Pat. No. 5,516,691) significantly complicate fabrication and incompletely address underlying transport limitations. They also lack the ability to orient hepatocytes in a more organotypic laminar configuration.

In recent years several designs for devices for culture of liver cells that address a subset of eight critical factors limiting the performance of hollow fiber-based LADs have been described. U.S. Pat. No. 5,658,797 describes a device for treating hepatocytes cultured on plate-like, gas-permeable slides. However, this device has a complicated radial geometry and requires culture of these cells within a complicated and otherwise restricting sandwich between collagen gels. U.S. Pat. No. 6,228,607 describes improvements to the concepts introduced in U.S. Pat. No. 5,658,797 by change to a Cartesian geometry for flow; however, limitations in the configuration of the culture and requirement of a liquid-permeable membrane intervening between perfusate and cells complicate its application. International PCT Application Publication No. WO 00/78932 addresses the above limitations by describing modular devices in which hepatocytes are cultured on gas-permeable, liquid-impermeable films in direct contact with perfusate. No means for loading cells by perfusion as a closed system or for changing volume of the chamber for cell culture without compromising sterility are disclosed, however, in this latter application. All of the above disclosures also do not fully address the configuration of systems for interfacing an extracorporeal LAD with a patient in liver failure and in need of treatment.

SUMMARY OF THE INVENTION

The invention features modular chambers for culturing cells in which the volume of the chamber can be adjusted without compromising the seal or sterility of the chamber. The invention is based on the principle that the volume of a chamber formed between two substantially rigid plates, in which the separation between plates is set by a substantially incompressible stop, can be adjusted using a gasket that forms a fluid-tight seal between the plates at a plurality of levels of compression. The invention enables the culture of cells in a chamber with a compartment that has a relatively large volume for seeding cells but a relatively small holdup volume for perfusion, such that this reduction in volume is made without opening or otherwise disassembling the chamber to compromise its liquid-tightness and sterility.

The new closed, modular, and scalable cell-culturing chamber can be thus perfused and used to culture cells (e.g., hepatocytes) with high levels of cell function in organ (e.g., liver) assist systems, for production of cells or cell-derived products (e.g., proteins or viruses) or for systems to treat biological liquids to remove toxins (e.g., ammonia), add cell-synthesized products, or both. When one or a plurality of chambers are seeded with the appropriate cells and are incorporated into a device, the device can be used to treat a patient with an organ (e.g., liver) in need of functional assistance.

The invention features methods for culturing cells, wherein the chamber is converted between two or more different configurations, wherein each configuration is distinguished by a unique distance between top and bottom plates corresponding to a unique volume in the compartment formed, without compromise of the liquid-tight and sterile seal formed by the gasket between the plates.

The invention features a chamber with gaskets that can be compressed to two or more different levels of compression while forming a seal that does not permit channeling across the gasket and does not fail mechanically under applied loads necessary for sealing. The gasket is retained and aligned in a groove in the top wall, bottom wall, or both walls of the compartment. The groove has a depth less than the thickness of the gasket and a width greater than the thickness of the gasket but not so great that the gasket tilts within the groove.

In one embodiment the gasket is made of closed-foam silicone sponge.

In one embodiment the gasket is an inflatable tube in which the internal pressure is maintained but the volume of gas inside varied to change the volume of the compartment.

In one embodiment the surface of the gasket is treated to allow the gasket to wet or adhere better to one or more of the walls of the compartment.

The invention features a chamber with fasteners to supply the applied load to the gasket for sealing. In one embodiment these fasteners are captive or quarter-turn fasteners that enable quicker tightening and loosening than standard machine screws. The number of fasteners required is a function of the mechanical properties of the gasket and walls of the chamber.

The invention features a chamber with adjustable volume, wherein a set of one or more substantially incompressible stops set the spacing between top and bottom walls and, thus, the volume of the compartment for each configuration.

In one embodiment the stops are substantially incompressible strips of metal or plastic. Tabs extending outside the edges of the top and bottom plates can be included to enable removal and exchange of shims to convert between different configurations with different volumes.

In one embodiment the stops are substantially incompressible bolts. The bolts can be colinearly located with fasteners securing the top and bottom plates together.

In one embodiment bowing of the top and bottom plates is minimized by locating the stops along the same centerlines as the fasteners used to supply an applied load.

In one embodiment bowing of the top and bottom plates is minimized by using two or more stops located in- and out-board, respectively, of the gasket.

In one embodiment springs are used with fasteners to maintain a minimum applied load on the gasket during use of the chamber and conversion between configurations with different volumes.

In one embodiment the surface in the chamber for cell attachment and culture is a gas-permeable, liquid-impermeable film. The gas-permeable liquid-impermeable film can be made of, e.g., polystyrene and also can be treated, e.g., by corona discharge.

In one embodiment the film is treated on the side for cell culture by coating with collagen prior to seeding cells.

The concentration of oxygen supplied to the chamber can be varied to control the function of the cells. Oxygenation can be through the surface for cell culture, through the medium, or by both methods.

The invention also features a method for tensioning a film on a backing. The backing can be a solid, porous, or perforated plate that is substantially rigid. The film tensioned on the backing can be used as a surface for cell culture in the chamber of the invention.

In one embodiment a film is tensioned on a backing, wherein the film and backing have different coefficients of thermal expansion, by adhering the film and backing together at a temperature higher than the temperature at which the composite of film and backing will be used in the chamber for cell culture.

In one embodiment a film is tensioned on a backing using an adhesive that is warmed to enable a thin coating of adhesive to form between the film and backing.

The invention features a chamber with adjustable volume that has two openings, wherein one opening is used to introduce a biological liquid into the chamber and another opening is used to vent the gaseous contents of the chamber during introduction of the liquid.

In one embodiment the chamber has two sets of a pair of openings, wherein one set is used for seeding the chamber in the chamber's larger volume configuration, and the other set is used for perfusing the chamber in the chamber's smaller volume configuration.

In one embodiment the ports for seeding cells into the chamber are distributed to uniformly distribute cells onto the surface for cell culture.

In one embodiment a plurality of ports are distributed and manifolded to uniformly distribute a biological liquid for perfusion through the compartment of the chamber.

In one embodiment slits between manifold for introducing and removing a biological liquid uniformly distribute the perfusing biological liquid through the compartment of the chamber.

The invention also features a chamber with adjustable volume for cell culture including a housing with a cell compartment comprising a liquid inlet and a liquid outlet formed by a gas-permeable, liquid-impermeable film and a liquid-permeable membrane, and a liquid compartment comprising a liquid entry and liquid exit formed by an impermeable wall and the liquid-permeable membrane, and wherein the liquid inlet and liquid outlet are arranged such that liquid entering the liquid inlet flows into the liquid entry and through the liquid-perfusion compartment and exits the liquid-perfusion compartment through the liquid exit and the housing through the liquid outlet.

The chamber can be seeded with cells, including adhesion-dependent cells and cells of mammalian origin. These cells can be from human, porcine, bovine, canine, feline, equine, ovine, rabbit, rat, or murine donors or from cultivated cell strains or cell lines from one or more of these donors. Additionally, the chamber can be seeded with hepatocytes. Cells are seeded onto the surface for cell attachment and culture.

The invention also features a method for seeding cells into the chamber as a closed system, wherein the cells suspended in a biological liquid are perfused through tubing into the chamber from a vented vessel, and the gaseous contents of the chamber vented from the chamber. The cells can be cultured in the chamber statically or under perfusion with a biological liquid.

In one embodiment the method for seeding cells into the chamber as a closed system is used to coat the surface for cell culture with collagen prior to seeding cells.

The invention features a method for culturing cells using the chamber with adjustable volume, wherein the cells are seeded into the chamber configured to accept a large volume of biological liquid, the cell-seeded chamber converted to a configuration with a smaller volume, and the cells perfused.

In one embodiment the closed system for seeding cells is created using a sterile tubing welder to make aseptic connections.

In one embodiment a plurality of chambers are manifolded together in parallel, series, or a combination thereof for perfusion. The individual chambers can be in configurations with identical or different volumes and can have either one or two compartments. Additionally, the chambers can be arranged to enable stacking of one chamber on top of another chamber.

In one embodiment the cells are preserved. Preservation can be by cryopreservation, hypothermic storage, or lyophilization.

In one embodiment, the nutrient-containing culture medium is perfused.

The invention also includes a liver assist system including (1) a flow-through device comprising one or more chambers with adjustable volume, each seeded with hepatocytes and manifolded at their inlets and outlets to common inlet and outlet manifolds, respectively; (2) a first conduit for conducting blood plasma from a patient to the inlet manifold; (3) a second conduit for conducting treated plasma from the flow-through device to the patient; and (4) one or more pumps for moving plasma through the conduits and flow-through device. The system can further include a plasma separator to remove blood cells from whole blood to provide plasma that is passed through the flow-through device.

In one embodiment the liver assist system of the invention includes a plasma exchanger that mixes and exchanges plasma between the patient, the plasma separator, and the flow-through device. The plasma exchanger can be a vessel with a single compartment or can have a plurality of compartments separated by liquid-permeable membranes. The liquid-permeable membranes have pores hindering transport of molecules with molecular weights greater than 50,000 to 100,000.

In one embodiment for the liver assist device of the invention, the plasma exchanger is an immunoisolation device.

In one embodiment for the liver assist device of the invention, a first conduit conducts plasma from the plasma separator to the inlet manifold to the chambers, and a second conduit conducts plasma from the outlet manifold of the chambers to the patient.

In one embodiment the liquid-permeable membranes separating cell and liquid compartments in a two-compartment chamber have pores hindering transport of molecules with molecular weights greater than 50,000 to 100,000.

The invention also includes a method of treating blood plasma including seeding a flow-through device for cell culture of the invention with hepatocytes, introducing blood plasma into the liquid inlet of the device, and allowing the plasma to flow through the device and exit through the liquid outlet.

The invention also includes a method for treating a patient in need of liver assist. The method includes attaching the liver assist system of the invention to the blood flow of a patient and treating the patient.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The novelty of the apparatus is the scalable culture of cells between substantially parallel, rigid flat plates in which a relatively large volume can be used to seed the cells, and the holdup volume reduced for perfusion, without opening or otherwise disassembling the system to compromise its liquid-tightness and sterility.

The invention is useful because it is desirable to seed as many cells as possible, albeit at a relatively low cell density to provide sufficient medium for cell support, and minimize the holdup volume of a chamber to minimize hemodilution during treatment yet provide sufficient cells for efficacy. Further, the ability to change from a configuration for seeding to a configuration for perfusion without extensive handling or compromising of sterility while forming sterile connections with a sterile tubing welder reduces handling time, reduces the need for expensive equipment for aseptic processing (e.g., biological safety cabinets or laminar flow hoods), and offers opportunities for aseptic processing at clinical sites.

The new flow-through devices for cell culture also allow various cells to be cultured with desirable levels of mass transport of oxygen and other nutrients, waste products, and beneficial products, while potentially reducing detrimental shear stress normally associated with higher levels of flow of medium. As a result, even relatively shear-sensitive cells such as hepatocytes can be cultured for extended periods of time at relatively low flow rates for medium with high levels of function. As a consequence, oxygenation and perfusion can be controlled independently. Further, these devices allow direct treatment of surfaces for promotion of cell attachment and function as well as more uniform distribution of cells within the devices in the form of laminar cultures that simulate the in vivo architecture of the liver. These features allow the new flow-through devices for cell culture to be used in organ (e.g., liver) assist systems.

Other features and advantages of the invention will be apparent from the following detailed description, and from the claims.

BRIEF DESCRIPTION OF THE DRAWINGS

FIGS. 1a and 1b are schematic diagrams of a closed chamber with adjustable volume for cell culture and organ assist, sealed with a compressible gasket, converted from a relatively highvolume configuration (1a) to a relatively low-volume configuration (1b) by exchange of a substantially incompressible shim.

FIGS. 3a and 3b are schematic diagrams of one embodiment of a closed cell-culturing chamber, sealed with a reversibly inflatable gasket, converted from a relatively high-volume configuration (3a) to a relatively low-volume configuration (3b).

FIGS. 6a and 6b are schematic diagrams of one embodiment of a closed cell-culturing chamber including a liquid-permeable membrane separating a perfusion compartment from a cell compartment in which a relatively high-volume cell compartment (6a) is converted to a relatively low-volume cell compartment (6b).

FIG. 7a is a schematic diagram of a system in which the flow rate through the chambers is independent of the flow rate of blood or plasma from and to the patient. FIG. 7b is a schematic diagram of a system in which the flow rate through the chamber depends on the flow rate of blood or plasma from and to the patient.

FIG. 9a is a schematic diagram of the parts of the unassembled chamber (viewed upside-down) showing its components, FIG. 9b is a schematic diagram of the assembled chamber (viewed upside-down), and FIG. 9c is a schematic diagram of the assembled chamber (viewed right-side-up).

FIG. 12a is a schematic diagram of the parts of the unassembled chamber showing its components, FIG. 12b is a schematic diagram of the assembled chamber in its configuration with expanded volume for seeding cells, and FIG. 12c is a schematic diagram of the assembled chamber in its configuration with reduced volume for perfusion.

DETAILED DESCRIPTION

Figure 2:
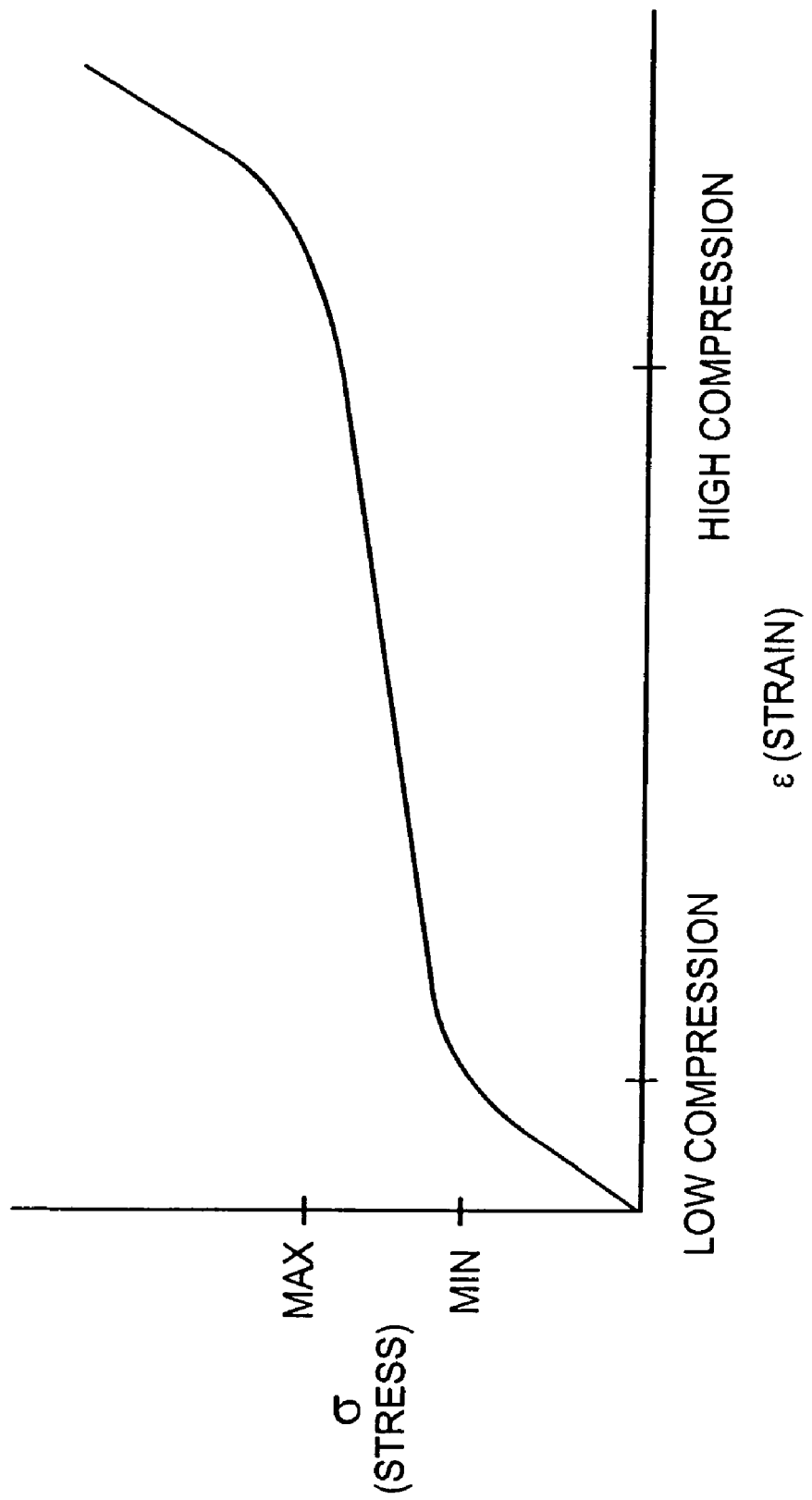
FIG. 2 is a design curve of the mechanical properties desired for gaskets for the invention in the form of a graph of stress as a function of strain.

The new chamber for cell culture enables the culture of relatively large numbers and high densities of adherent cells (e.g., hepatocytes) on substantially rigid surfaces in chambers in which the volume of the chamber can be adjusted without compromising the seal or sterility of the apparatus and the geometry of the chamber can be controlled precisely to set the volume of the chamber and the hydrodynamic shear stresses to which the cells are subjected. Thus, the invention allows: (1) the chamber to be seeded with cells and these cells cultured in a relatively large volume of medium, and then (2) the cells to be perfused in the same chamber but with the chamber's holdup volume reduced. The chamber is easy to handle and operate, as it allows loading of cells by perfusion as a closed system and changes in volume by simple adjustments of fasteners with screwdrivers and exchange of substantially incompressible stops. The chamber also is scalable and modular, provides for culture of cells on a taut, gas-permeable, liquid-impermeable support in which transport limitations are reduced by separating flow of perfusing medium (for supply of nutrients and soluble toxins and/or inducers, and removal of wastes and metabolic byproducts) from oxygenation, and facilitates incorporation into flow circuits for treatment of patients in liver failure.

FIGS. 1a and 1b show one embodiment of the new chamber 10 that includes a compartment 20 defined by a top wall 30 and a bottom wall 330 with sidewalls formed by a compressible gasket 50 that creates a liquid-tight seal between the top and bottom walls and isolates the compartment from the external environment. The seal formed by the gasket is held in place by a set of fasteners 70 with corresponding receptacles 80, such that liquid held inside the compartment is unable to leak out of the compartment and contaminants (e.g., bacteria and mycoplasma) in the external environment are unable to penetrate through the seal and into the compartment. The contents of the compartment are cells 130, substantially cultured on the bottom wall and in contact with a biological liquid 15, such as medium for cell culture, blood, plasma, or a balanced salt solution, that completely fills the compartment and provides aqueous support for the cells.

The top wall 30 is typically composed of a cell-compatible, liquid-impermeable material such as anodized aluminum, stainless steel, other metallic alloys, or substantially incompressible plastic (e.g., polycarbonate, polystyrene, and Teflon®) and their composites. These materials can be used for other device components including fittings and manifolds. The bottom wall is composed of a substantially rigid and planar material or composite with a surface 320 facing the interior of compartment 20 that promotes, supports, or otherwise does not interfere with the attachment and culture of cells 130. It typically is desirable to make the thickness of the top and bottom walls as small as possible without otherwise prohibiting the fabrication of these parts, the rigidity of the assembled chamber, and the operability of the chamber for cell culture so as to reduce the overall weight of the chamber and facilitate its handling. For these reasons anodized aluminum is useful as a material of construction because of its relatively light weight for its strength, its ease of machining, and its biocompatibility for cell culture.

In one embodiment the chamber 10 exists in one of two or more configurations, each configuration being distinguished by a unique volume of the chamber's compartment established by the height between the top wall 30 and the bottom wall 330. FIG. 1a depicts the one-compartment chamber in its relatively high-volume configuration, henceforth termed the "seeding" configuration, with a relatively large compartment to hold cells 20. FIG. 1b depicts the chamber in its relatively low-volume configuration, henceforth termed the "perfusion" configuration, with a smaller compartment to hold cells. Additional configurations with different volumes also are permitted. The substantial parallel alignment between top and bottom walls remains identical between the seeding configuration and the perfusion configuration (as well as any additional configurations), with the geometry of the compartment changing between configurations only by the distance between the top and bottom walls.

The chamber is converted between the different-volume configurations by changing the applied load and compression on the gasket 50. The higher-volume seeding configuration of FIG. 1a requires that the gasket forms a liquid-tight and sterile seal between the compartment 20 and the external environment at a relatively low level of applied load and compression; the lower-volume perfusion configuration of FIG. 1b requires that the gasket also form a liquid-tight and sterile seal between the compartment 20 and the external environment at a higher level of applied load and compression. Applied load typically is measured and denoted as σ, stress, with units of force per unit area. Compression typically is measured and denoted as ε, strain, with dimensionless units.

The gasket 50 is composed of one or more materials that have mechanical compatibility with the applied loads that must be supported and with the volumes for each configuration. The applied loads for each configuration must be great enough that the gasket compresses to form a seal that withstands the pressure exerted by the biological liquid 15 within the compartment 20 for that configuration. For static configuration this pressure is given by the gravity head formed by the biological liquid within the compartment. For perfused configurations or configurations involving perfusion, this pressure is given by a combination of the gravity head and the pressure drop associated with flow of the biological liquid. The minimum and maximum applied loads correspond to the applied loads for the configurations with the largest and smallest volumes, respectively. The volumes for each configuration are the product of the planar areas exposed to the compartment by the top wall 30 and bottom wall 330 and the height of the compartment in that respective configuration.

FIG. 2 depicts a design curve for the mechanical properties desired in a gasket 50 for the new chamber 10. As with any seal-forming material, the gasket must be compressible and not contain passages that permit channeling of fluid from one side of the seal to the other. In particular, the material must support the applied load necessary for each level of compression corresponding to a configuration for the chamber. This requirement means that it is desirable that the gasket must be relatively compliant, such that the ratio of change in applied load necessary to convert between configurations and the change in level of compression between these configurations is relatively small. The smaller this ratio is, the wider the range of volumes that can be accommodated in the compartment 20 of the chamber.

The gasket 50 also must be stiff over a range of applied loads and compressions without "mechanically failing." Mechanical failure means that the material for the gasket cracks or otherwise loses its structural integrity, such that it no longer can support the applied load and no longer can form a liquid-tight and sterile seal. Mechanical failure typically is associated with the relatively large and unbounded increase in applied load required as the level of compression increases significantly beyond the high level of compression shown in FIG. 2. Reversibility, in the form of being able to repeatedly switch between states of low applied load and compression and states of high applied load and compression, is desirable for gaskets but not required.

It is possible that a material that is not a composite is suitable for use as the gasket 50 for the new chamber 10. However, materials suitable for use as the gasket 50 for the new chamber more typically are composites of two or materials in which one component is relatively stiff and the other component is relatively compliant. Specific materials meeting the mechanical requirements for the gasket outlined above include closed-foam sponges, such the silicone, neoprene, reinforced silicone, and fluorosilicone rubber materials distributed by Greene Rubber Company, Inc. (Woburn, Mass.), closed-pore polyurethane foams, and reversibly "energized" gaskets.

FIG. 3 illustrates one embodiment of an energized gasket as an inflatable closed tube 170. FIG. 3a shows a chamber in its seeding configuration in which a gas within the gasket tube 170 is pressurized to inflate the tube, such that the gasket tube is relatively filled with gas, is stiff, and forms a liquid-tight and sterile seal between the top wall 30 and the bottom wall 330. The volume and pressurization of the gas within the tube is controlled with a regulator. By adjusting this regulator to maintain the pressurization of the gas within the tube while changing the volume of gas within the tube, the distance between top and bottom walls can be changed while the seal is maintained. For example, by decreasing the volume of gas within the tube in this manner, the chamber in seeding configuration depicted in FIG. 3a can be converted to the chamber in perfusion configuration, with compartment 20 with smaller volume, as depicted in FIG. 3b.

It is useful to provide a groove to retain the gasket at different levels of compression without compromising the liquid-tight and sterile seal formed by the gasket between the compartment 20 and the external environment as well as to align the gasket for assembly and proper operation. FIG. 1 shows that the gasket 50 and FIG. 3 shows that the gasket 170 is seated in a groove 310 formed in the top wall 30. It also is possible that a groove for the gasket is formed in the bottom wall 330 or in both top and bottom walls. The depth of the groove must be chosen to be less deep than the height of the gasket in its uncompressed state and provide desired levels of compression at corresponding applied loads to support two or more levels of compression and, thus, volume configurations. The width of the groove must be greater than or equal to the width of the gasket and provide sufficient volume for the gasket upon the gasket's greatest level of compression, where sufficiency for this volume is a function of the Poisson's ratio for the gasket. In particular, the groove should not be too wide as to allow misalignment of the gasket within the groove or to allow the gasket to tilt within the groove such that the levels of compression desired for the different volume configurations can not be reliably attained.

In another embodiment the surface of the gasket is treated, such that the gasket better wets or adheres to the groove 310, the top wall 30, the bottom wall 330, or a combination thereof. This treatment can be chemical, physical, or a combination of chemical and physical. The treatment increases the robustness of the seal while also promoting retention and alignment.

The volume of the compartment 20 has no inherent upper limit, as by choosing different combinations of thickness of the top wall 30 or bottom wall 330 with thickness and type of gasket 50, any conceivable minimum level of compression can be attained for a desired minimum applied load. The different levels of compression for the different volume configurations are determined by the distance between the top and bottom walls and maintained by a set of one or more substantially incompressible stops.

In one embodiment, depicted in FIG. 1, one or more substantially incompressible shims 60 and 160 act as the stops to set the level of compression, applied load, and volume for each different volume configuration. In this embodiment shims of different thickness are removed from the periphery of the fasteners 70, inserted around the periphery of the fasteners, or exchanged with other shims to convert from relatively high-volume configurations to relatively low-volume configurations and vice-versa. The thickness of the shim determines the level of compression and the height of the chamber's compartment. In particular, FIG. 1a depicts the seeding configuration with a relatively thick shim 60, termed the outer seeding shim, used to set the spacing between top wall 30 and bottom wall 330 for the compartment 20. FIG. 1b depicts the perfusion configuration with a relatively thin shim 160, termed the outer perfusion shim, used to set the spacing between top and bottom walls for the compartment.

Preferably, spacing between top and bottom walls for each configuration is determined, at least partially, by a set of four of more shims, each of identical thickness, lying out-board of the fasteners, such that the shims can be installed and removed or exchanged from the sides of the chamber without twisting or otherwise damaging individual shims. Further, shims preferably have dimensions in the plane of the chamber that extend outside the edges of the top wall 30 and bottom wall 330, such that each shim has a tab that allows the shim to be grasped or pulled from the chamber to facilitate removal of the shim upon conversion of configuration. Alternatively, for one or more configurations the spacing between top and bottom walls is determined by a single piece of substantially incompressible material acting as a shim, in which this shim is intended to be either (1) installed during assembly and not removed during operations except upon conclusion of use of the chamber and cleaning or (2) changed irreversibly (e.g., by cutting or otherwise breaking into a plurality of parts) during removal or exchange in the process of converting from one configuration to a second configuration with a different volume.

Figure 4A:
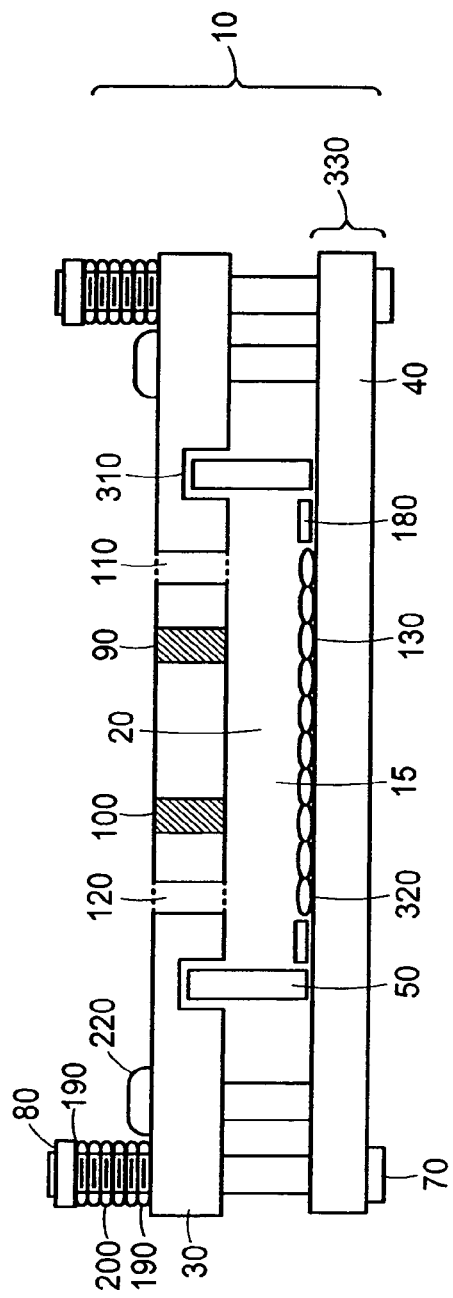
FIGS. 4a and 4b are schematic diagrams of a closed cell-culturing chamber converted from a relatively high-volume configuration (4a) to a relatively low-volume configuration (4b) by removal of distributed substantially incompressible bolts of fixed length while a minimum stress is applied to the seal using springs.
Figure 4B:
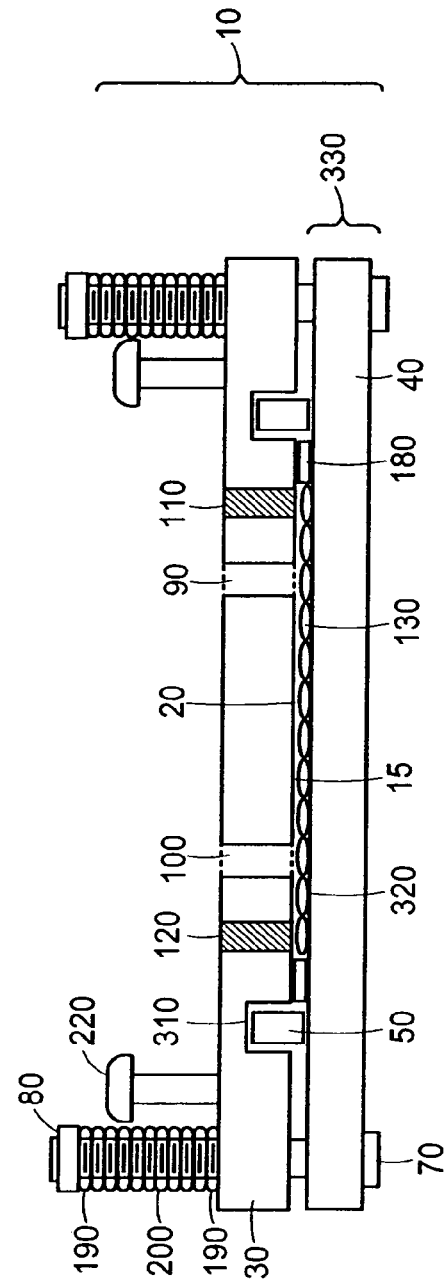

In another embodiment, depicted in FIG. 4, substantially incompressible bolts 220 with defined lengths act as the stops to set the level of compression, applied load, and volume for a specific volume configuration. In this embodiment these bolts are tightened fully to set the height of the compartment 20 for the seeding configuration of FIG. 4*a* and loosened for the perfusion configuration of FIG. 4*b*, such that in this latter configuration these bolts do not touch the bottom wall 330 and the spacing between the top wall 30 and the bottom wall is set by a shim 180, termed the "inner shim," that lies within the compartment 20 and is bounded by the gasket 50. This inner shim is present in the seeding configuration but does not touch both the top and bottom walls simultaneously at points on the opposing faces of the shim, such that it does not set the spacing between top and bottom walls in the seeding configuration. It also is possible that the substantially incompressible bolts extend through the bottom wall and touch the face of the top wall within the seeding compartment 20, such that these bolts protrude from the external face of the bottom wall upon loosening. Combinations of bolts passing through the top wall and bolts passing through the bottom wall also are anticipated.

Specific materials suitable for substantially incompressible outer and inner shims include thermoplastics (e.g., polycarbonate), metals (e.g., aluminum and stainless steel), and composites of rigid materials. There is no lower limit for the thickness of the shims, although in practice a thickness greater than 0.001" is desired. Similarly, specific materials suitable for substantially incompressible bolts 220 include thermoplastics, metals, and composites of rigid materials. The length of the bolts is determined by their manufacture.

In the design of the new chamber 10 it is desirable to minimize bowing of the top wall 30 and bottom wall 330 upon tightening of fasteners 70. Bowing can result if a net torque is applied on either or both of these walls due to the gasket 50 acting as a fulcrum for the applied load supplied by the fasteners for sealing. This torque creates a moment that typically increases the volume of the compartment 20 because the fasteners are located out-board of the gasket. In general, bowing is undesirable because it is difficult to reproducibly set, results in variances in the spacing between walls and, thus, spacing between top and bottom walls of the compartment within an individual chamber, and results in variances in holdup volume for a given configuration between different chambers constructed identically.

Bowing can be reduced by colinearly locating the fasteners supplying the applied load and the substantially incompressible stops setting the space between top and bottom walls. For example, in one embodiment bowing is minimized by using substantially incompressible shims with fingers interlacing between fasteners. These fingers act to balance the torque created by having the fasteners out-board of the gasket 50. Alternatively, as illustrated in the embodiment depicted in FIG. 4*a*, bowing can be reduced by locating substantially incompressible stops 220 on the same centerline as the fasteners 70. Combinations of these two embodiments also are possible.

In the embodiment shown in FIG. 4 springs 200 are used to maintain a defined minimum applied load on the gasket 50 during all operations, including conversion between different volume configurations. In this embodiment fasteners 70 are retained by receptacles 80, with each spring retained by a pair of washers 190 around each fastener. FIGS. 4*a* and 4*b* show the springs lying above the top wall 30; alternatively, the springs can lie beneath the bottom wall 330. This embodiment has the advantage that continuous application of a non-zero applied load guarantees preservation of the liquid-tight seal and, thus, sterility for the compartment 20.

The springs 200 have mechanical properties such that, at the each level of compression, the springs provide sufficient or greater-than-sufficient applied load for that volume configuration. For example, in the seeding configuration depicted in FIG. 4*a*, the springs supply a relatively high applied load, possibly greater than the minimum applied load required for this configuration. However, in the perfusion configuration depicted in FIG. 4*b*, the springs supply a relatively lower applied load that nonetheless is equal to or greater than the applied load required for this configuration.

The springs 200 can be made from any material that does not experience plastic deformation over the range of applied loads needed for the different volume configurations and corresponding levels of compression. Materials that are suitable for the spring include stainless steel and other metals. The most critical property for the spring is its elastic modulus or Hookean constant, which must be chosen with regard to with the applied loads and length of the fasteners 70.

For embodiments not containing springs to supply a minimum applied load, changing the applied load and level of compression to convert between configurations is accomplished by either loosening the fasteners 70 in FIGS. 1 and 3 to reduce the level of compression and increase the volume of the chamber's compartment or tightening these fasteners further to increase the level of compression and decrease the volume. Alternatively, for the embodiment with springs of FIG. 4, loosening the bolts 220 from their tightened configuration of FIG. 4*a* to their less tightened configuration of FIG. 4*b* results in the conversion of the chamber 10 from the relatively high volume seeding configuration to relatively low volume perfusion configuration. For this latter embodiment the fasteners are used-to set the initial compression on the springs and not adjusted subsequently.

The number of fasteners 70 required is determined by the width and thickness of the gasket 50, the mechanical properties of the top wall 30 and bottom wall 330, and the applied loads required for sealing this gasket without inducing bowing in the top and bottom walls. For ease of handling and operation it is desirable that these fasteners seat in receptacles 80 such that fewer turns are required for tightening and loosening each fastener than with standard machine screws. The desired applied load for a particular volume configuration determines the extent to which the fasteners must be tightened or loosened for any specific configuration. The fasteners for the new chamber 10 are relatively nonintrusive, very easy to operate, unlikely to fail, and inexpensive to obtain and operate.

Specific embodiments for fasteners 70 and receptacles 80 for the new chamber 10 depicted in FIG. 1 include captive and quarter-turn fasteners from Southco® (Concordville, Pa.), Rexnord Specialty Fastener Division (Hasbrouck Heights, N.J.), and Dzus Fastener Co., Inc. (West Islip, N.Y.) and other forms of latches that allow quick application and release of compression between parts. The use of pins for alignment, composed of a material such as anodized aluminum or stainless steel, that are integral to the top wall 30 or bottom wall 330 can facilitate alignment of these walls with fasteners and receptacles during assembly of the chamber.

Cells 130 in the new chamber 10 may attach on any surface inside the compartment 20, but it is preferred that the cell mass be substantially cultured on the surface 320 of the bottom wall 330 facing the compartment and that this surface serves as a support for cell culture. Materials having the following characteristics provide suitable surfaces for use in the new chamber: relatively non-cytotoxic to cells on at least the side facing the compartment (such that the attachment and function of the cells is not limited by the material or that the material can be surface treated on this side such that the attachment and function of the cells is not limited by this surface-treated side of the material) and relatively non-degrading in the presence of the biological liquid 15. Materials having these characteristics can be easily obtained commercially or prepared using standard techniques. As described in International PCT Application Publication No. WO 00/78932, the disclosure of which is incorporated herein by reference, surface treatment to promote cell adhesion and desired cell function may be chemical treatment, such as by non-specific coating with collagen and/or other molecules and/or by covalent attachment of specific molecules favoring cell culture, by physical treatment such as corona discharge in the presence of an oxygen-bearing gas (e.g., air), or by any combination thereof.

For many applications in cell culture, control of oxygenation of cells and their supporting medium is beneficial for regulating cell function. In the culture of some types of cells, oxygenation is by the medium for cell culture. However, other types of cells, such as hepatocytes, have demands for oxygen that are characteristically high. The function of viable hepatocytes also can depend on tension of oxygen presented to the cells. For example, increasing the concentration of oxygen from ambient (19%) to 40% increases ureagenesis by almost 50%. Another consideration which intensifies the need for oxygenation in a cell culturing or organ assist device is the need to incorporate relatively large numbers and high densities of cells into the device while limiting volume of biological liquid.

In one embodiment the cells 130 are cultured on a gas-permeable, liquid-impermeable planar support 320 through which the cells exchange gas such as oxygen with the oxygenated environment (e.g., air, which is 19% oxygen) external to the chamber. As disclosed in International PCT Application Publication No. WO 00/78932, this embodiment is useful and desirable for many types of cells, including hepatocytes for use in a LAD. Such a cell culture support must be impermeable to liquid under pressures encountered in operation but permeable to oxygen in the range from about 0.1 mL/m$^2$/day to about 1000 L/m$^2$/day.

In order to retain the mechanical rigidity necessary for the bottom wall 330 as well as permit permeability of gases, enable sterilization, be resistant to puncture, ripping, and wrinkling, and be able to be handled during manufacture of the chamber, it is preferred that this bottom wall be a composite of a thin, gas-permeable and liquid-impermeable film 320 supported on a thicker, porous or perforated rigid support or frame 40. In particular, this frame mechanically supports the film yet is either sufficiently permeable, porous, or spatially distributed such that the frame presents no additional significant limitations to gas transport, particularly for oxygen, and also has the requisite mechanical properties, such that the frame does not otherwise impact the effective permeability of the film. For example, the use of impermeable posts (not shown) relatively widely spaced to support the film satisfies these requirements. However, precise control of volume for the different volume configurations requires also that the film be taut and not sag under pressures encountered in use.

In one embodiment the bottom wall is a film-frame assembly formed by tensioning a gas-permeable, liquid-impermeable film onto a perforated metal frame. Tensioning is achieved by taking advantage of differences in coefficients of thermal expansion between the film and the frame and by decreased viscosity and increased ability to spread of the adhesive used to bond the film and frame. The coefficient of thermal expansion is the ratio of the change in length of a material per unit length per degree Celsius. When a film has a greater coefficient of thermal expansion than the frame, the film contracts more than the frame upon lowering of temperature. Thus, applying an adhesive between the film and frame warmed to an elevated temperature and allowing the adhesive to set at this elevated temperature, the film contracts more than the frame upon restoration to a lower temperature, resulting in the film becoming taut. The degree of tautness depends on the relative differences in coefficients of thermal expansion between the film and frame and the difference between the ambient and elevated temperatures. This method also requires the use of an adhesive that is compatible with both film and frame and with elevated temperatures.

Figure 5:
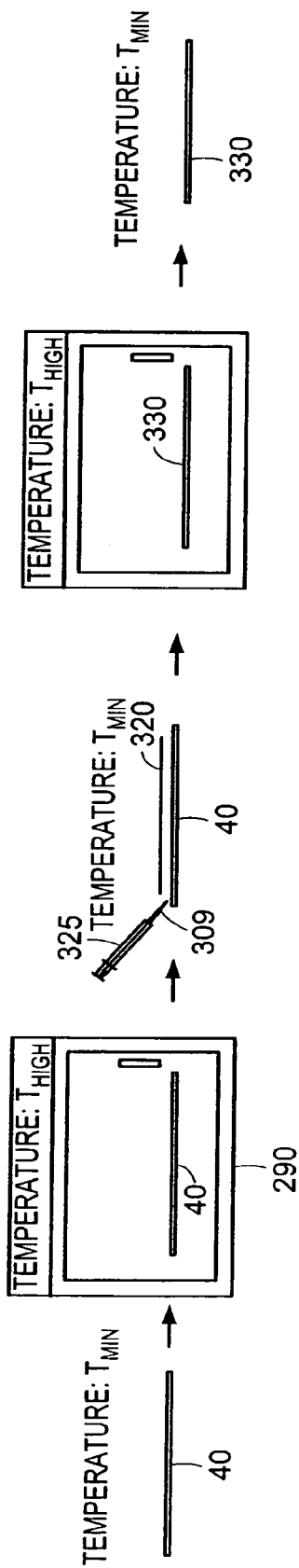
FIG. 5 is a schematic of a process for tensioning films onto a backing based on differences in the coefficient of thermal expansion between film and backing.

It is well known that the viscosity of most materials decreases as temperature increases. FIG. 5 shows that an adhesive can secure the film 320 to the frame 40 by tightly binding the film and frame, such that tautness achieved by differences in coefficients of thermal expansion are maintained upon cooling. Further, a thin, uniform line or layer of adhesive is necessary to prevent bumps in the joint where the adhesive binds the film and frame; these bumps can compromise the seal formed between the gasket 50 and the film-frame assembly 330 as well as produce unevenness in the spacing between top wall 30 and film-frame assembly. Such non-uniformities could contribute to non-uniform flow in the chamber in perfusion configurations depicted in FIGS. 1b, 3b, and 4b. Thus, the adhesive preferably is applied by syringe with tapered tip 309 or other such device that delivers the adhesive as a thin coating that minimizes the spacing between the frame and film. Further, the adhesive is applied to a frame that has been warmed, such that the heat available in the frame heats the adhesive and increases the ability of the adhesive to spread as a thin coating. Alternative methods for applying the adhesive also are possible, including (1) spraying the adhesive onto the film, perforated frame, or both and (2) using an adhesive tape applied to the parts.

FIG. 5 depicts the process for tensioning a film 320 to a frame 40 to form a film-frame assembly 330 with a taut film. The frame first is warmed to a temperature above the ambient room temperature of typically 18-22° C. and above the temperature of 37° C. at which the film will be used as a support for cell culture in a chamber, a thin line of adhesive 325 applied by dispensing from a syringe with tapered tip 309 onto the surface of the frame to be in contact with the film, the film laid onto the frame such that the side of the film to be facing away from the cells 130 in the compartment of the chamber is in contact with adhesive and the frame, and the new film-frame assembly transferred back to an oven or incubator 290 held at a temperature above the temperature to be used for cell culture for a period of time sufficient to set the adhesive. The elevated temperature for treatment of the adhered film on the frame can be the same as the temperature used to heat the frame prior to application of the adhesive or, preferably, a higher temperature to promote better spreading of the adhesive, quicker binding of adhesive to film and frame, and/or increased tensioning of the film due to differential coefficient of thermal expansion with regard to the frame. Then, upon removal of the film-frame assembly from the oven or incubator, the film contracts to a tautness.

Materials for films having the necessary characteristics for this method and consistency with other characteristics described above can be easily obtained commercially or prepared using standard techniques. In one embodiment the film is non-porous polystyrene, in the form of a sheet of Polyflex®, 0.002"-thick film of polystyrene manufactured by Plastics Suppliers, Inc. (Columbus, Ohio). For this embodiment, with a frame 40 composed of anodized aluminum, the adhesive 325 preferably is an epoxy, and even more preferably a medical grade epoxy, such as the medical grade epoxy EP21LV from Master Bond, Inc. (Hackensack, N.J.), the temperature for warming the frame is 40° C., and the temperature for treatment of the film-frame assembly 330 is 45° C.

In the new chamber the biological liquid in the chamber's compartment supplies cells with basic nutrients for cell culture and carries away metabolites. The biological liquid also supplies the cells with toxins, aminated molecules, and other biological waste products to be metabolized and carries away detoxified products, secreted factors, and proteins. For in vitro culture of cells this biological liquid preferably is a medium designed for cell culture. For ex vivo treatment by the cells this biological liquid preferably is plasma, blood, or component thereof.

Biological liquids preferably are supplied to and removed from the compartment in the new chamber through two openings, one serving as an inlet for supplying the compartment and another opening serving as an outlet to discharge or drain the compartment. More preferably, there are two types of these pairs of openings, as shown in FIGS. 1, 3, and 4: a first type of opening 110 and 120 used for seeding cells 130 from a suspension in the relatively high-volume seeding configuration depicted in FIGS. 1a, 3a, and 4a, and a second type of opening 90 and 100 for perfusing cells with biological liquids in the relatively low-volume perfusion configuration depicted in FIGS. 1b, 3b, and 4b. The openings communicate between the interior and exterior of the compartment by a port or manifold. Ports can be connected with cavities of other chambers in parallel, in series, or both to create a flow circuit or loop for the seeding of cells, perfusion of a biological liquid, or rinsing or aspirating the contents of the compartment. The addition of other ports can serve as vents for displacement of air during filling or as a means of draining the compartment when the other ports are attached to those of another chamber.

The openings for supply and removal of biological liquids preferably are distributed so as to uniformly supply the new chamber with the biological liquids. It is preferable that cells are seeded from a suspension of cells in biological liquid such that the cells uniformly distribute through the chamber and attach as a uniform culture onto the culture support. For the relatively large chambers permitted by this invention, such uniform loading preferably is facilitated by having one or more ports for introducing the suspension of cells located toward one end or side of the chamber and another set of one or more ports for venting the air displaced from the compartment upon introduction of the suspension of cells located at the opposite end or side of the chamber from the first set of ports. Venting of air is facilitated by tilting the chamber so that the ports for venting are above the horizontal plane of the ports for introducing the suspension.

The openings for supply and drainage of biological liquids for perfusion also preferably are distributed so that the flow of liquid within the chamber's compartment is uniform. Uniformity is defined as the hydrodynamic shear stress at any horizontal position is substantially constant and the flow does not move substantially slower or faster in any section of the main body of the compartment. Studies with hepatocytes demonstrate that ureagenesis is independent of hydrodynamic shear stresses up to at least 2 dynes/cm$^2$.

To create uniform flow of a perfusing biological liquid (also termed perfusate), it is preferable that a plurality of openings be used to introduce the biological liquid to be perfused into the compartment for the chamber in the chamber's perfusion configuration and that a plurality of openings be used to remove the biological perfusate from the compartment. More preferably, the openings for introducing the perfusate to the compartment are manifolded, such that, from a single common inlet, a manifold distributes the perfusate uniformly to individual ports for uniform distribution into the compartment. Similarly, it is preferable that the openings for removing the perfusate from the compartment are manifolded, such that a separate manifold (distinct from the manifold for the inlet) collects the perfusate uniformly from a second set of individual ports (distinct from the first set of ports for the inlet) for removal from the chamber through a single common outlet.

Another method for achieving uniform flow of a perfusate within the compartment of the chamber is to create a thin slit between the inlet manifold and the compartment and a similar thin slit between the compartment and outlet manifold. The length of the slit preferably is the length of the compartment, and the width of the slit preferably is substantially smaller than the diameter of the manifold.

Creation of uniform flow of a perfusing biological liquid within the chamber can be visualized and evaluated by introducing a colored or otherwise detectable dye into the perfusate and observing the distribution of dye within the compartment. An alternative method for evaluating the flow of perfusate through the chamber is based on measuring the pressure drop across the chamber (i.e., the difference in pressure between the inlet for perfusion to the chamber and the outlet for perfusion to the chamber). Measured pressure drops can be compared with pressure drops predicted by models from fluid mechanics (e.g., as described in Denn, *Process Fluid Mechanics*, Prentice-Hall, Inc., Englewood Cliffs, N.J., 1980) as a means to clarify whether patterns of flow are ideal or how much these patterns differ from ideal. In particular, preferably the flow in the manifolds and compartments is laminar, such that the flow is well characterized and has a Reynolds number less than 2000.

Based on such observations and basic concepts from fluid mechanics, guidelines can be formulated to direct the design of ports and manifolds. For uniform distribution of perfusate from the inlet manifold into a plurality of inlet openings into the compartment within the chamber in the chamber's configuration for perfusion and from the compartment through a plurality of outlet openings into the outlet manifold, it is preferable that the cross-sectional area of the respective manifolds be greater than or equal to the sum of the cross-sectional areas of the plurality of corresponding openings. Thus, changing the number and/or diameter of the inlet and/or outlet openings and/or the diameter of the corresponding manifold to follow this guideline facilitates uniform supply and drainage of perfusate from the compartment. Alternatively, the effective cross-sectional area for the inlet manifold can be reduced numerically by supplying the perfusate to the inlet manifold from two or more inlet openings to the chamber. Similar consequences result for corresponding actions on the outlet manifold.

Because some cells have attachment or functional properties which are affected adversely by direct contact with a flowing biological liquid and are shear sensitive, in some applications it may be desirable to place a liquid-permeable membrane between the flowing biological liquid and the cells to limit hydrodynamic interactions. In this arrangement an additional compartment, a cell compartment, is incorporated into the chamber to interact with a compartment with a flow biological liquid.

FIG. 6 shows one embodiment of a two-compartment chamber for cell culture having an impermeable top wall 30, a bottom wall 330 that supports attachment and culture of cells 130, a compressible gasket 50 that creates a liquid-tight seal between the top and bottom walls, at least one liquid-permeable membrane 240 separating a compartment for cells 130 from a compartment for perfusion 260, and sidewalls 250 for the compartment 260. The compartment for cells is defined by the bottom wall, the gasket, and the liquid-permeable membrane. The compartment for perfusion is defined by the liquid-permeable membrane, the sidewalls 250, and the top wall. The volume of the compartment for perfusion is the mathematical product of the area of the liquid-permeable membrane in contact with both the compartment for cells and compartment for perfusion and the height of the sidewalls. To minimize volume of the compartment for perfusion it is preferable that the sidewalls be composed of a relatively thin and substantially incompressible shim.

Although FIG. 6 depicts the two-compartment chamber divided such that the compartment for perfusion 260 is above the one or more liquid-permeable membranes 240, the chamber can be oriented in any direction as long as the compartment for cells 20 intervenes between the liquid-permeable membrane and the bottom wall 330. FIG. 6 depicts the use of fasteners 70 and mating receptacles 80 to secure the assembled chamber and supply the applied load on the gasket 50. However, springs with washers also can be used with fasteners and receptacles to supply a constant minimum applied load, as described in one embodiment above.

In one embodiment the chamber 10 exists in one of two or more configurations, each configuration being distinguished by a unique volume of the compartment for cells 20 established by the height between the liquid-permeable membrane 240 and the bottom wall 330. FIG. 6a depicts the two-compartment chamber in its seeding configuration, with a relatively highvolume compartment for cells 20. FIG. 6b depicts the chamber in its perfusion configuration, with a relatively low-volume compartment for cells. As with the one-compartment chamber described in an embodiment above, additional configurations with different volumes also are permitted. For each configuration, however, the volume of the compartment for perfusion 260 preferably remains constant, although it is permissible to also change the volume of this latter compartment. The substantial planarity between top wall, liquid-permeable membrane, and bottom wall remains identical between the seeding configuration and the perfusion configuration (as well as any additional configurations), with the geometry of the compartment for cells changing between configurations only by the distance between the liquid-permeable membrane and bottom walls.

The two-compartment chamber is converted between the different volume configurations by changing the applied load and compression on the gasket 50. The higher-volume seeding configuration of FIG. 6a requires that the gasket form a liquid-tight and sterile seal between the compartment for cells 20 and the external environment at a relatively low level of applied load and compression; the lower-volume perfusion configuration of FIG. 6b requires that the gasket also form a liquid-tight and sterile seal between the reduced-volume compartment for cells and the external environment at a relatively high level of applied load and compression. The volumes for the compartment for cells are set by substantially incompressible stops, which can be either shims and/or bolts as described for previous embodiments above, as depicted in FIGS. 1, 3, and 4. Conversion between configurations is as described above for other embodiments, with method of conversion dependent on whether shims or bolts are used as stops and whether springs are used to supply a minimum applied load on the gasket.

The compartment for perfusion 260 contains a second biological liquid 132, such as medium for cell culture, a balanced salt solution, blood, or plasma. The compartment for cells 20 contains both cells 130 substantially cultured on the bottom wall 330 as well as a biological liquid 15 that may be the same or different from the second biological liquid 132 in the compartment for perfusion. The biological liquids 15 and 132 are in liquid contact through the intervening one or more liquid-permeable membranes 240. The biological liquid-15 supplies the cells with basic nutrients for cell culture, toxins, aminated molecules, and other biological waste products to be metabolized and carries away cell metabolites, detoxified products, secreted factors, and proteins. These molecules are transported across the liquid-permeable membrane to and from the biological liquid 15.

The biological liquid 15 in the compartment for cells 20 flows very slowly or is static. The flow of the first biological liquid 15 is substantially unaffected by the flow of the second biological liquid 132 in the compartment for perfusion 260. The second biological liquid 132 preferentially is initially supplied to the compartment for cells 20 during filling and is free to exchange with the biological liquid 15 across the liquid-permeable membrane 240. During seeding with a suspension of cells the first biological liquid 15 preferably is supplied to and removed from the compartment for cells through two openings, one opening 110 serving as an inlet for supplying the compartment and another opening 120 serving as an outlet for to discharge or drain the compartment. The biological liquid 132 preferably is supplied to the compartment for perfusion through a second, independent set of two openings, one opening 90 serving as an inlet for supplying a perfusing biological liquid and a second opening 100 serving as an outlet for the perfusing biological liquid. Each opening communicates between the interior and exterior of its corresponding compartment by a port or manifold. Ports can be connected with corresponding compartments of other chambers in parallel, in series, or both to create separate flow circuits or loops for the seeding of cells from a suspension and for the perfusion of the second biological liquid 132 or for rinsing or aspirating the contents of each compartment. The addition of other ports can serve as vents for displacement of air during filling or as a means of draining a compartment when the other ports communicating with the compartment are attached to those of another chamber.

In the embodiment featured in FIG. 6 the openings for supply and removal of biological liquids 15 and 132 are distributed so as to uniformly supply each compartment of the two-compartment chamber with its corresponding biological liquids. For the compartment for cells 20 the cells 130 preferably are seeded from a suspension such that the cells uniformly distribute through the compartment and attach as a uniform culture onto the culture support 330. For the relatively large chambers permitted by this invention, such uniform loading preferably is facilitated by having one or more ports 110 for introducing the suspension of cells located toward one end or side of the chamber and another set of one or more ports 120 for venting the air displaced from the compartment 20 upon introduction of the suspension of cells located at the opposite end or side of the chamber from the ports 110. Venting of air is facilitated by tilting the chamber so that the ports for venting are above the horizontal plane of the ports for introducing the suspension.

In one embodiment the openings for supply and drainage of the perfusate are distributed so that the flow of liquid within the compartment for perfusion is uniform. For a two-compartment chamber the flow rates and hydrodynamic shear stresses allowed in the compartment for perfusion are bounded by the mechanical compliance and strength of the liquid-permeable membrane, with higher flow rates and shear stresses preferable for mixing. To create uniform flow of the perfusate, a plurality of openings preferably are used to introduce the biological liquid to be perfused into the compartment for perfusion, and a plurality of openings used to remove the perfusate from the compartment. More preferably, the openings for introducing the perfusate to the compartment for perfusion are manifolded, such that, from a single common inlet, an inlet manifold distributes the perfusate uniformly to individual ports for uniform distribution into the compartment for perfusion. Similarly, it is preferable that the openings for removing the perfusate from the compartment for perfusion are manifolded, such that a separate and distinct outlet manifold collects the perfusate uniformly from individual ports for removal from the chamber through a single common outlet. Guidelines for sizes of ports, openings, and manifolds for this embodiment are identical to the guidelines discussed above for other embodiments.

The chamber is seeded with functional cells. Preferably, the chamber (or the compartment for cells for a two-compartment chamber) in its relatively large-volume, in its seeding configuration is seeded with cells from a suspension of cells, with the bottom wall acting as a support for cell culture. Further, for use as an organ assist device the seeded cells preferably function together to simulate the types and levels of function possible for cells in an organ. Cells can grow in the chamber, remain stable in number, or switch between modes of growth and numerical stability. Cells also can maintain their previous phenotype or change phenotype upon culture in the chamber. The chamber can be used as an in vitro culture system and/or as an organ assist device to treat a patient in need of organ assistance.

One source of cells for the chamber is a mammalian organ. When this organ is the liver, the cells that are cultured for use in a LAD comprise hepatocytes, the principal cells of the liver which are capable of fulfilling the functional requirements typically associated with the liver when placed in an appropriate chemical and structural environment. Other cells present in liver also may be included in the chamber acting as a LAD, such as endothelial cells, Ito cells, Kupfer cells (specialized macrophage-like cells), and fibroblasts. A co-culture of hepatocytes with one or more of these or other types of cells may be desirable in a LAD. For devices comprising a plurality of chambers, each chamber may be seeded with the same numbers of cells and/or combinations of types of cells or different numbers and/or combinations.

Given the relatively limited availability of human cells, non-human sources of cells can be used in the invention. Cells from other mammals including, but not limited to, porcine, bovine, equine, canine, feline, ovine, and murine sources can be used. Donors for cells can vary in development and age, sex, species, weight, and size. Cells may be derived from donor tissues of embryos, neonates, or older individuals including adults. Embryonic progenitor cells such as parenchymal or mesenchymal stem cells can be used in the invention and induced to differentiate to develop into the desired tissue. In addition, mixtures of cells from different cell strains, mixtures of normal and genetically modified cells, and/or mixtures of cells from two or more species or tissue sources may be used.

An alternative source of cells is by culturing either cells previously obtained from a mammalian organ or by culturing cells that have been previously cultured such that they exist as a cell line. Cells for use in the invention may be normal or genetically engineered by spontaneous, chemical, or viral transfection. Recombinant or genetically engineered cells can be created for immortality, reduced allogenicity, or differentiated hepatocyte function. Procedures for genetically engineering cells are generally known in the art; and are described in Sambrook et al., *Molecular Cloning, A Laboratory Manual,* Cold Spring Harbor Press, Cold Spring Harbor, N.Y., 1989.

Cells are seeded from fresh, processed tissue, from cells cultured previously in vitro, thawed from cryopreserved tissue, or some combination thereof. Prior to seeding, cells are suspended in a seeding medium and the bottom wall containing the surface for cell culture treated, if desired, to promote attachment and function of cells as described above. Treatment of this surface may be conducted prior to assembly of the chamber or subsequent to assembly of the chamber. When surface treatment is conducted subsequent to assembly of the chamber, the treatment is applied, if it is in the form of a fluid, through the inlets and outlets for seeding cells.

Cells are seeded into the chamber (or the compartment for cells for the two-compartment chamber with liquid-permeable membrane) in its seeding configuration by pumping a suspension of cells directly into the device without direct exposure to the external environment. The flow rate for delivering the suspension of cells is rapid enough to prevent settling and other deterioration of cells within the circuit for delivery yet slow enough to prevent substantial mechanical damage to cells or clumping due to hydrodynamic shear. This flow rate depends on the size of the tubing, and in practice the critical property for delivery is the hydrodynamic shear stress on the walls of the tubing for delivery. Preferably, the shear stress to which the walls of the system for delivery are exposed is between 0.1 and 3.0 dynes/cm$^2$. The suspension of cells preferably is delivered to the compartment in the chamber via one or more ports so that both the time and shear stress for delivery are minimized while favoring more uniform distribution of cells into the compartment.

Subsequent to delivery into the chamber, the cells are allowed to settle and attach for a period sufficient to establish a culture of cells, typically no less than 6 hours and no more than 24 hours. At this point in time the biological liquid used to seed the cells is removed by opening a pair of ports and using one of these ports for aspirating the biological liquid under a vacuum and the other port for venting the chamber to allow air to displace the biological liquid. The chamber in seeding configuration then is converted to a chamber in perfusion configuration as described above, primed with a biological liquid for perfusion, and perfusion of the chamber initiated. This set of procedures enables seeding of cells in a relatively large volume of biological liquid-typically, $5 \times 10^6$ cells per mL of base culture medium, although higher densities of cells are possible but less preferable-and subsequent perfusion with a four-fold reduction in holdup volume for the chamber and with minimal disassembly or exposure to the external environment.

Two specific embodiments are possible for the environment in which a chamber is seeded with cells. For either embodiment all parts are sterilized (e.g., by steam autoclaving, gamma irradiation, or a chemical treatment such as exposure to hydrogen peroxide) prior to assembly into the chamber and peripheral circuits within a biological safety cabinet (BSC) that provides an aseptic (i.e., free of biological contaminants) environment. Alternatively, the chamber may be assembled from non-sterile parts and the assembled chamber then sterilized—by one of the above methods—as a unit.

In one embodiment the chamber is processed entirely within a BSC. In an alternative embodiment the chamber is processed without further use of a BSC by using instead a sterile tubing welder to make to make aseptic connections (by a hot knife or microwave or UV radiation), in a relatively unclean environment, between segments of PVC-based tubing with plugged ends to prevent contamination. Preferably, a SCD® IIB, SCD® 312, or TSCD® tubing welder from Terumo Medical Corporation (Somerset, N.J.) is used to reliably create and break sterile connections. Experiments have shown no difference in performance between chambers handled solely using BSCs and chambers processed using a SCD® IIB tubing welder. The ability to change a chamber from seeding configuration to perfusion configuration without extensive handling or compromising of sterility while forming sterile connections with a tubing welder facilitates reduced handling time, reduces the need for expensive equipment for aseptic processing (e.g., BSC or other types of laminar flow hoods), and offers opportunities for aseptic processing at clinical sites (thus widening possibilities for cryopreservation).

Because of the unitary nature of the new chamber for cell culture, the chambers are scalable with the addition of surface area and volume to the compartments or the addition of a plurality of chambers. In the case where additional chambers are incorporated, it is preferred that the compartments communicate via the ports to allow perfusion of a biological liquid between them. For this communication the inlet 90 for biological liquid is connected to an external inlet manifold that distributes the flow of the biological liquid evenly to each of the plurality of compartments to expose cells (or compartments for perfusion for two-compartment chambers) to the biological liquid. After passage through the multiple compartments in parallel, the biological liquid is collected in a common external outlet manifold.

The manifolds for this multi-compartment chamber for cell culture preferably are connected to their associated compartments by detachable connectors. These connectors allow easy installation and possible replacement of individual connections. Alternatively, the external inlet and outlet manifolds may be, if desired, permanently connected to each associated compartment.

For a device consisting of a plurality of individual chambers, each chamber may be seeded with cells either together with other chambers in the assembled state or seeded with cells separately as individual chambers not bundled together with external inlet and outlet manifolds and then subsequently manifolded together into a complete system. The time at which seeded chambers are assembled together in this latter embodiment may be soon after seeding or after allowing further establishment of cultures.

Cells seeded in the chamber can be preserved. Preservation can be by cryopreservation, hypothermic storage, or lyophilization.

When the cells seeded are hepatocytes and/or other cells from a liver, the new chambers in perfusion configuration can be used as a LAD to treat an individual in need of liver assistance. In general, the LAD consists of one or more of the chambers, a means to obtain blood from the patient for treatment, and a means to exchange the blood with the contents of chambers so as to allow the cells to treat the blood or components thereof. The LAD can be used to treat a human or other animal in liver failure.

In general, at least two types of embodiments are possible for configuring the set of one or more chambers, the patient, the means to obtain blood from the patient, and the means to exchange the patient's blood with the chambers: a circuit in which the flow rate through the chambers is independent of the flow rate of blood or separated plasma from the patient, and a circuit in which the flow rate through the chambers is matched to the flow rate of blood or separated plasma from the patient. The first configuration is termed henceforth as a LAD with complete recycle, and the second configuration is termed henceforth as a LAD with single pass.

Figure 7A:
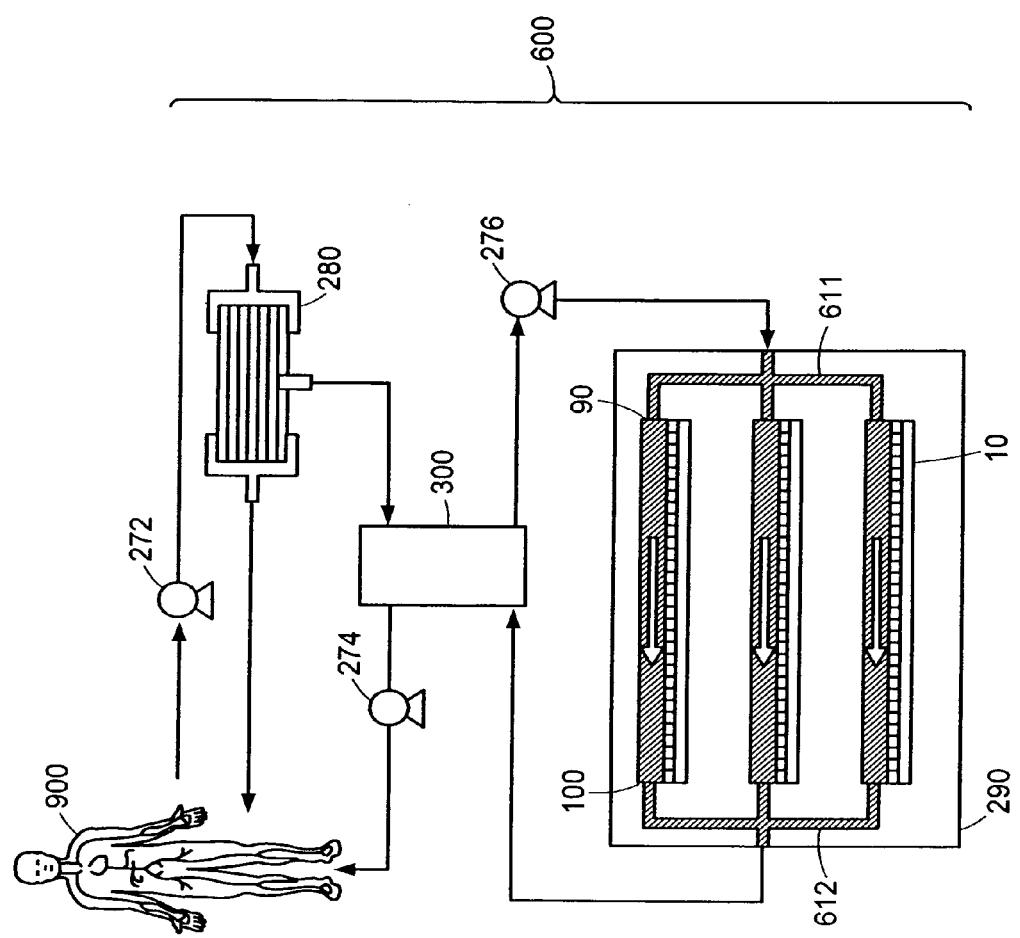
FIGS. 7a and 7b are schematic diagrams of two embodiments of the use of a plurality of cell-seeded closed chambers with adjustable volume as part of an organ assist system in which a patient in organ failure is treated with the cells in the chamber.

FIG. 7a shows a schematic diagram of an embodiment for an extracorporeal liver support system in which the new chambers 10 for cell culture are used as part of a LAD with complete recycle. The system includes an incubator 290 with multiple chambers in perfusion configuration (such as the chambers depicted in FIGS. 1b, 3b, 4b, and 6b). Housed inside the incubator is an external inlet manifold 611 for distributing biological liquid to the inlets for perfusion 90 for each chamber and an external outlet manifold 612 for collecting biological liquid from the outlet for perfusion 100 for each chamber. Biological liquid is supplied to the external inlet manifold from a plasma exchanger 300 by a pump 276 and returned from the external outlet manifold to the plasma exchanger. Blood from the patient 900 is supplied by a pump 272 into a plasmapheresis unit 280, in which plasma is separated from blood concentrated in cell components. The separated plasma then flows into the plasma exchanger, where it is mixed with the biological liquid treated by the cells cultured in the chambers. The concentrated blood is returned directly back to the patient. Some of the contents of the plasma exchanger also are returned to the patient by a third pump 274 to convey the treated plasma to the patient. Within the flow of the biological liquid and plasma are also monitors for pH, temperature, and flow sensors (not shown).

The extracorporeal liver support system 600 depicted in FIG. 7a is termed a LAD with complete recycle because the contents of the chambers 10 are not returned directly to the patient 900 after each pass through the chambers but rather recycled and mixed with plasma from the patient in the plasma exchanger 300. The chambers preferably are manifolded in parallel, although it is possible to manifold one or more of the chambers in series. The number of chambers can vary up to 100 or more, and the chambers can be loaded with identical or different cells as well as with identical or different numbers of cells. Further, the chambers can be identical in number of compartments, or some of the chambers can have only a single compartment and some of the chambers two compartments with one or more intervening liquidpermeable membranes.

The plasma exchanger 300 in the LAD with complete recycle 600 functions as a mixer for the plasma generated from the patient by the plasmapheresis unit 280 and the biological liquid treated by the cells in the chambers 10. The plasma exchanger can exist in one of two embodiments. In one embodiment the plasma exchanger is a simple container that allows free mixing of the plasma from the plasmapheresis unit and the biological liquid from the chambers with other mixing limitations. The composition of the liquid in the plasma exchanger in this embodiment is determined simply by rules of mixing of two completely miscible liquids based on the volume of the plasma exchanger and the flow rates of plasma generated by the plasmapheresis unit, of treated biological liquid generated by the manifolded chambers, and of liquid from the plasma exchanger pumped to the chambers and to the patient. In this embodiment no immunoisolation exists between the cells in the chambers and the patient, unless the chambers each have two compartments with a liquid-permeable membrane that also functions as an immunisolating membrane.

The plasma exchanger 300 also may not be a simple container allowing free mixing of plasma from the plasmapheresis unit and biological liquid from the chambers but rather an immunoisolation device in which the mixing of fresh plasma from the patient and treated liquid from the chambers 10 is controlled by passage across membranes designed to prevent the passage of immunoreactive molecules. In the immunoisolation device the pool of plasma generated from and returned to the patient are separated from the pool of biological liquid treated by the chambers and supplied to the chambers. With an immunoisolation device mixing between patient's plasma and biological liquid treated by the cells in the chambers is reduced relative to the free mixing permitted in the simple mixer of the previous embodiment. However, selection of cutoffs for membrane pore sizes for the immunoisolation device conveys benefits for immunoisolation not possible with the simple mixer of the first embodiment. These liquidpermeable membranes preferably have pores hindering transport of molecules with molecular weights greater than 50,000 to 100,000.

Figure 7B:
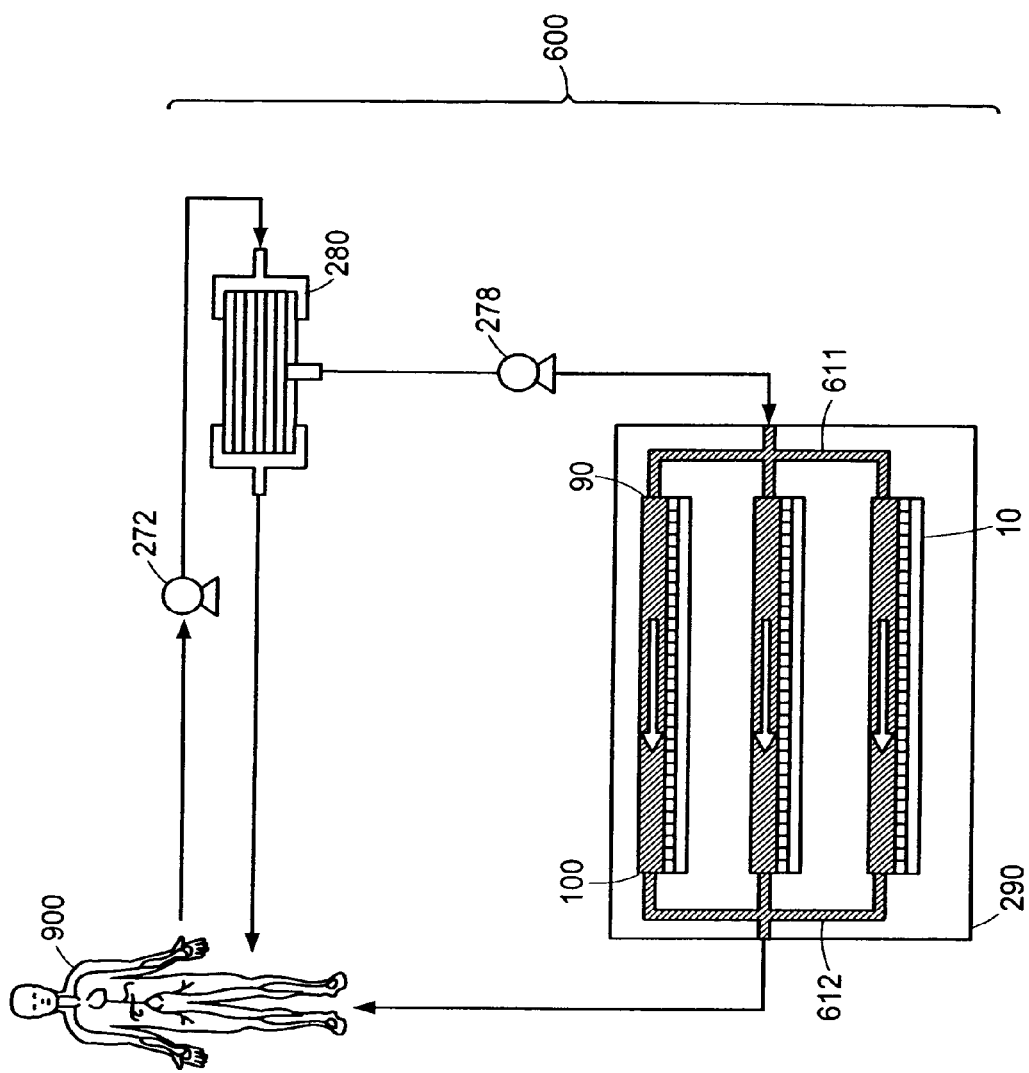

FIG. 7*b* shows a schematic diagram of an embodiment for an extracorporeal liver support system in which the new chambers for cell culture are used as part of a LAD with single pass. The system includes an incubator 290 with multiple chambers 10 in perfusion configuration (such as the chambers depicted in FIGS. 1*b*, 3*b*, 4*b*, and 6*b*). Housed inside the incubator is an external inlet manifold 611 for distributing plasma directly to the inlets for perfusion 90 for each chamber and an external outlet manifold 612 for collecting treated plasma from the outlet for perfusion 100 for each chamber. Blood from the patient is supplied by a pump 272 into a plasmapheresis unit 280. Separated plasma then is supplied to the external inlet manifold from a plasmapheresis unit 280 by a pump 278 and returned as treated plasma from the external outlet manifold directly to the patient 900. The concentrated blood again is returned directly back to the patient.

The extracorporeal liver support system 605 depicted in FIG. 7*b* is termed a LAD with single pass because the contents of the chambers 10 are returned directly to the patient 900 after only one pass through the chambers rather than recycled and mixed with plasma from the patient in a plasma exchanger. The chambers can be manifolded in parallel or in series, with the choice of configuration dependent on the desired mixing characteristics and kinetics of the cells for processing toxins. The number of chambers can vary up to 100 or more, and the chambers can be loaded with identical or different cells as well as with identical or different numbers of cells. Further, the chambers can be identical in number of compartments, or some of the chambers can have only a single compartment and some of the chambers two compartments with one or more intervening liquid-permeable membranes. Because the LAD with single pass 605 does not feature a plasma exchanger for mixing plasma generated from the patient with biological liquid treated by the chambers, the LAD with single pass cannot provide immunoisolation between patient and cells unless each chamber also has two compartments with at least one liquid-permeable membrane that functions as an immunoisolating membrane.

EXAMPLES

The invention is further described in the following examples, which do not limit the scope of the invention described in the claims. Example 1 describes the procedure for tensioning a thin polymeric film onto a perforated metal backing based on differential thermal expansion. Examples 2, 3, and 4 describe the assembly, seeding with cells, and perfusion of a closed cell-culturing chamber with adjustable volume in which volume is adjusted by exchange of substantially incompressible plastic shims. Example 5 describes one embodiment of the system in which a plurality of cell-seeded closed chambers with adjustable volume is used to treat a patient in organ failure. Example 6 describes assays used to measure hepatocyte function and evaluate the performance of closed cell-culturing chambers with adjustable volume. Examples 7 and 8 describe the performance of closed cell-culturing chambers with adjustable volume. Example 9 describes the assembly, seeding with cells, and perfusion of a closed cell-culturing chamber with adjustable volume in which a minimum load is maintained on the seal for the chamber using springs.

Example 1

Tensioning a Polystyrene Film onto a Perforated Metal Backing

Figure 8:
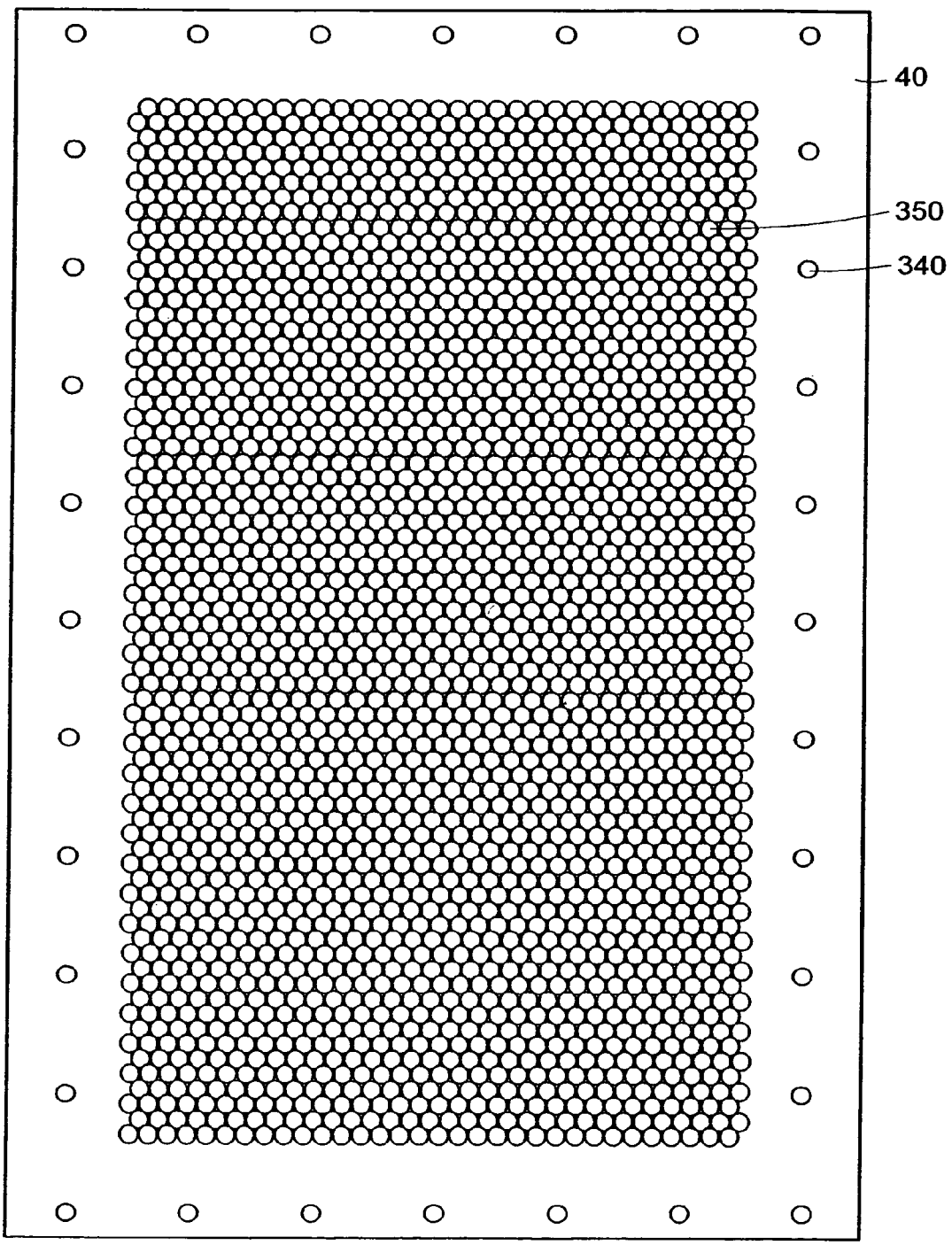
FIG. 8 is a schematic diagram of a frame with a plurality of holes, on which a gas-permeable, liquid-impermeable film is attached on the side facing the interior of the closed cell-culturing chamber.

The ability to attach and tension a thin polymeric film onto a perforated metal frame based on differences in coefficients of thermal expansion between film and frame was demonstrated using a 0.002"-thick film of polystyrene (Polyflex®, Plastics Suppliers, Inc., Columbus, Ohio) and an aluminum frame 40 (depicted in FIG. 8). This film, corona-treated on one side, provides a gas-permeable, liquid-impermeable surface onto which hepatocytes can be seeded, attach, and be cultured, as previously described in International PCT Application Publication No. WO 00/78932. The frame was prepared by machining a first set of 2240 0.252" diameter through-holes 350, spaced 0.272" diameter-to-diameter apart in a honeycomb-like pattern centered on the 12"×19" surfaces of a ¼"-thick aluminum jig plate (McMaster-Carr, Bridgeport, N.J.), and a second set of 52 0.252"-diameter through-holes 340 into the same surfaces along their perimeter. Subsequently, the frame was treated with a 0.0005-0.0008"-thick sulfuric anodization, Type II, clear per Mil-A-8625C, to protect against attack by solvents. This first set of holes 350 provided perforations for free exchange of gas across the film to be applied; the second set of holes 340 allowed the frame with attached film to be assembled with an opposing plate into a chamber for cell culture. The second set consisted of 2 groups of 21 through-holes arranged along the long axis of the frame, 0.825" from the adjacent edge of the frame along the frame's short axis and spaced uniformly with centers 0.916" apart, and two groups of five through-holes arranged along the short axis of the frame, 0.340" from the adjacent edge of the frame along the frame's long axis and spaced uniformly with centers 1.725" apart.

To form a film-frame assembly the perforated frame 40 first was warmed to 40° C. in an incubator and then briefly removed to apply a thin, approximately 0.003"-thick line of medical grade epoxy (EP21LV, Master Bond, Inc., Hackensack, N.J.), mixed at a 1:1 ratio by weight of parts A and B, on one of the faces of the frame containing the through-holes. This line of epoxy was applied by dispensing from a 10 mL-volume syringe with tip tapered to 0.027"-ID (Small Parts Inc., Miami Lakes, Fla.) and placed between the interior and exterior sets of through-holes, 350 and 340, respectively. A 10"33 18" film of Polyflex, corona side on the face of the film not opposing the frame, next was laid onto the epoxied side of the frame and the assembly incubated overnight at 45° C. The assembly was removed from the incubator and allowed to cool to room temperature, sections of the film exterior to the line of epoxy and towards the edge of the frame excised using a box cutter, and the assembly sterilized by gamma irradiation. This procedure resulted in a tensioned gas-permeable, liquid-impermeable film, suitable as a surface for attachment and culture of adherent cells, fixed onto a perforated metal backing that was substantially flat and did not substantially sag when assembled into a perfused chamber for cell culture.

Example 2

Closed Chamber with Adjustable Volume—Assembly and Seeding with Cells

Figure 9A:
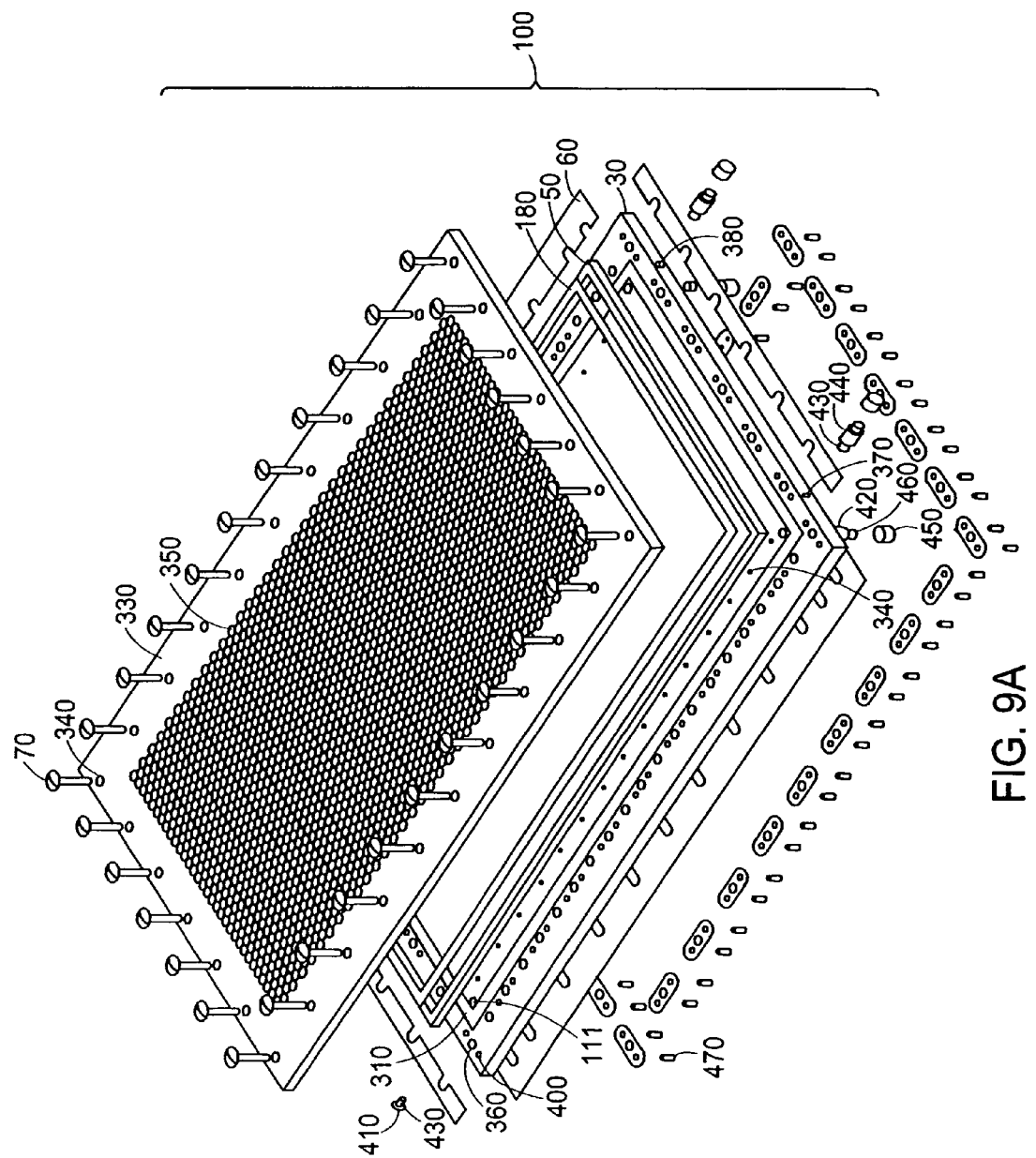
FIGS. 9a, 9b, and 9c are schematic diagrams of perspective views of a closed cell-culturing chamber in which volume is adjusted by exchange of substantially incompressible shims.
Figure 9B:
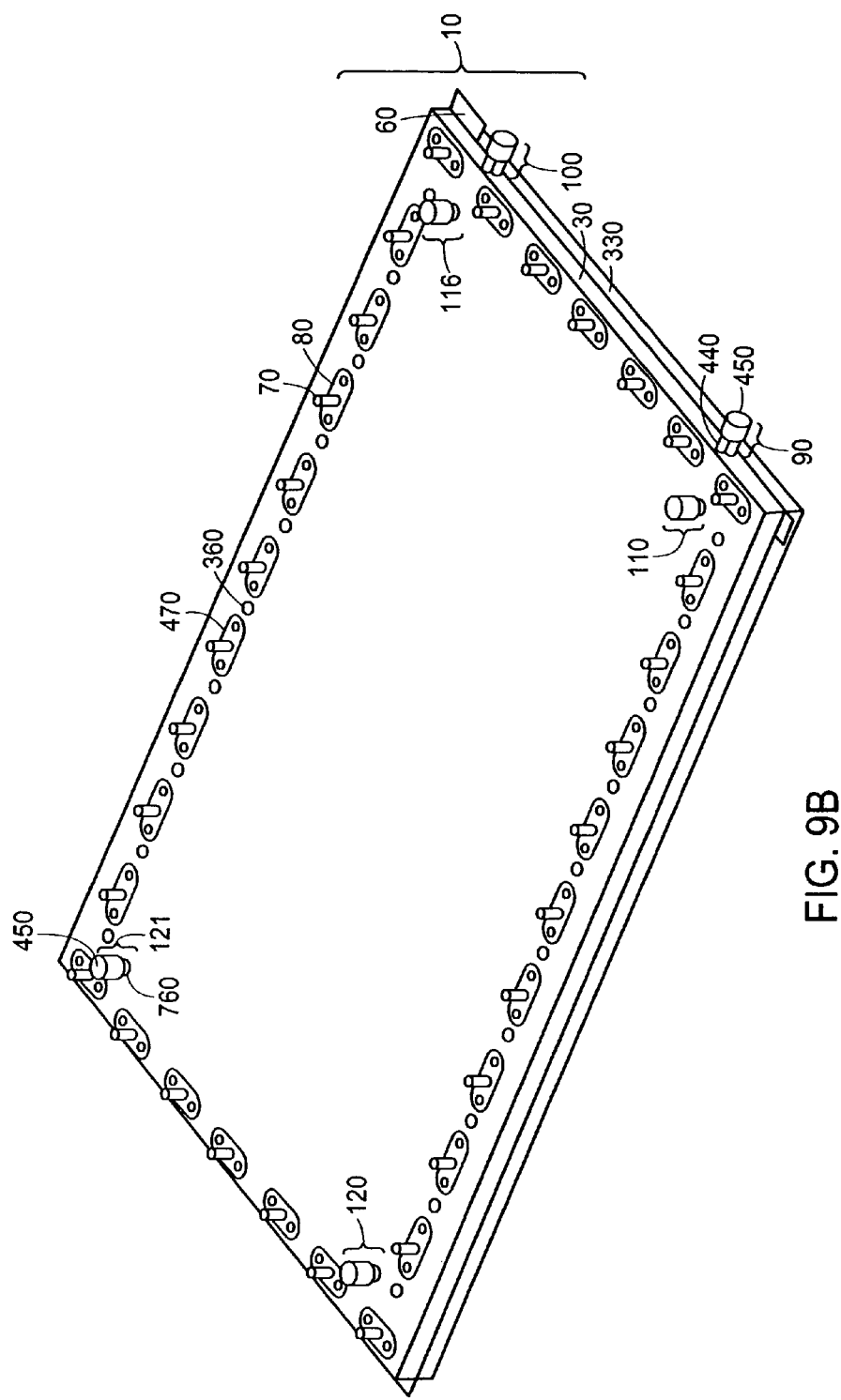
Figure 9C:
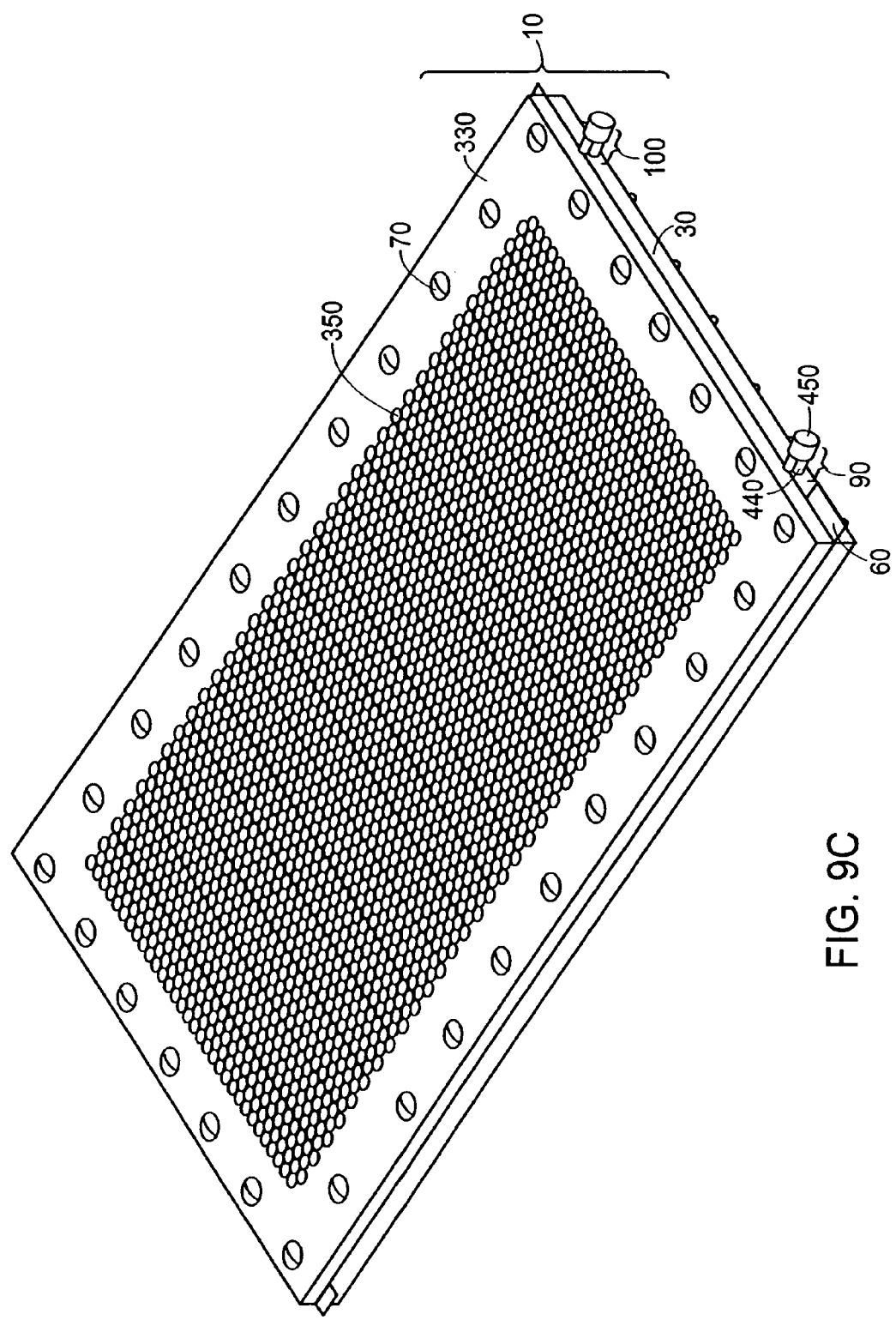

The ability of closed chambers with adjustable volume, in which the volumes are set by use of substantially incompressible shims, to be seeded with cells was evaluated by constructing a chamber. The chamber 10, as depicted in FIGS. 9a, 9b, and 9c, comprised an assembly of top plate 30, film-frame assembly 330, compressible gasket 50, substantially incompressible inner shim 180, sets of substantially incompressible outer shims for seeding 60 and for perfusion, associated fittings 410, 440, 450, and 460, and associated components 70, 80, 420, 430, and 470 for fastening the film-frame assembly to the top plate.

The top plate 30 was a piece of 12"×19"×⅜"-thick aluminum jig plate (McMaster-Carr) machined with a set of 6 types of features and finished with a 0.0005-0.0008"-thick sulfuric anodization, Type II, clear per Mil-A-8625C. A set of 32 0.257"-diameter, ⅜"-deep through-holes 360 matched the set of 32 through-holes 340 in the frame 40 of the film-frame assembly 330 and permitted passage of fasteners 70. These matching sets of through-holes were spaced to substantially distribute loading forces from fasteners for uniform sealing with the gasket. On one 12"×19" face of the top plate two 0.112"-diameter through-holes 400, tapped for #6-32 round-head stainless steel screws 470, were machined opposing a subset of the holes 360. On the opposite face of the top plate a 0.078"-deep, 0.375"-wide 17.914"×9.916" groove 310, centered on the face, provided a space for seating a ¼"-thick medium-grade silicone sponge rubber gasket (Greene Rubber, Woburn, Mass.). An additional four ⅜"-deep through-holes 111 (numbered clockwise from the face of the top plate without the groove), tapped for plastic #¼-28 threaded-to-male Luer-lock fittings 460, were machined in the top plate adjacent to the corners of the groove. These holes were counter-bored 0.346"-diameter on the face opposing the groove to allow use of size –009 O-rings 420 to seal between the fittings 460 and top plate. The combination of the fittings and the holes created a seeding port 110, a seeding/aspirating port 116, a vent port 120, and an extra port 121. These holes were used for introduction and removal of liquids in the relatively high-volume seeding configuration.

Introduction into and removal of liquids out of the relatively low-volume perfusion configuration was implemented by a manifold of relatively large-diameter inlet and outlet tubes and a set of smaller-diameter cross-holes. Two 19"-long 0. 155"-diameter through-holes 370 and 380, 1.843" from the adjacent sides and centered on the ⅜"-thick face, were machined along the long axis of the top plate. Each end of these holes were counter-bored 0.290" diameter×0.050" deep and tapped 0.200" deep to accept stainless steel #10-32 fittings 440 with associated –006 O-rings 430 to seal the fitting to the top plate. Finally, 30 0.025"-diameter, 0.110"-deep cross-holes 390 were punched into the face of the top plate with the groove to connect provide a passage for fluids from the 19"-long holes 370 and 380 to the top, with 15 holes 390 per 19"-long hole. These holes 390 were spaced uniformly 1.129" apart.

The chamber 10 was partially assembled by first fastening a set of 28 Southco® stainless steel receptacles 80 (D. B. Roberts, Boston, Mass.) onto the face of the top plate 30 opposing the groove 310 using the tapped holes 400 and two #6-32 round head stainless steel screws 470. These receptacles were not intended to be routinely removed from the top plate during disassembly and cleaning of the chamber after cell culture. Next, the four Luer-lock fittings 460 with O-rings 430 were loosely threaded into the corresponding tapped holes 111 and corresponding plastic female Luer-lock plugs 450 were tightened onto each of these Luer-lock fittings. The top plate then was flipped to expose the face with the groove 310, the gasket 50 aligned in the groove, and a 0.005" thick, 0.25" wide, 17.14"×9.14" polycarbonate inner shim 180 placed on top plate and bounded by the gasket. This partial top assembly was sterilized by steam autoclaving before further assembly. Pairs of #10-32 flat head stainless steel screws 410 and #10-32 threaded-to-male Luer-lock fittings 440, all with size –006 O-rings 430, also) were sterilized by steam.

All subsequent steps in assembly were conducted in a biological safety cabinet (BSC) and involved sterilized parts except as noted. Aseptic processing was insured by handling materials with either sterile tweezers or sterile gloves within the BSC. First, the film-frame assembly 330 and partial top assembly were unwrapped from their autoclave bags and loose fittings 460 tightened. Next, the film-frame and top assemblies were aligned by matching up the sets of through-holes 360 and 340, such that the film-bearing side of the film-frame assembly and the side of the top assembly with protruding gasket were opposing. Southco° fast lead threaded stainless steel screws 70 then were inserted from the exposed face of the film-frame assembly through the holes 360 and 340 and captured in the receptacles 80. A set of four 0.0625"-thick polycarbonate outer shims 60 were placed in between the screws to set the volume of the chamber 10 at 165 mL for seeding cells in the seeding configuration. These outer shims for seeding had planar dimensions that allowed them to extend outside the perimeter formed by the edges of the top plate 30 and film-frame assembly, as depicted in FIGS. 9b and 9c.

The chamber 10 then was sealed by tightening the Southco® screws 70, from inside to corners to uniformly compress the gasket 50 without inducing substantial bowing of the chamber, with a power screwdriver (Black & Decker, Hampstead, Md.) at minimum torque. The Southco® screws 70 subsequently were tightened further by repeating the above procedure with a setting of 3½ on the screwdriver's torque adjustment. The final step in the assembly of the closed chamber in the seeding configuration was installation and tightening of the fittings 440 and 410 onto the ends of the pair of 19"-long holes 370 and 380, such that each side of the chamber contained only one type of these two fittings. The chamber was maintained under aseptic conditions and not opened until use. This procedure resulted in the creation of a closed, sterile chamber in the seeding configuration in which cells could be seeded onto a 17.164"×9.166" area of gas-permeable, liquid-impermeable film within a sealed 165 mL-volume compartment.

Studies of the closed chamber 10 as a cell-culturing device were conducted using primary hepatocytes in base culture medium (Williams E medium supplemented with 4.5 g/L glucose, 0.5 U/mL bovine insulin, 7 ng/mL glucagon, 7.5 µg/mL hydrocortisone, 10 mM HEPES, 20 ng/mL EGF, 20 mM glutamine, 10 IU penicillin, and 10 µg streptomycin) with 1% horse serum (HS), obtained from livers of Yorkshire/Hampshire crossbred pigs (EM Parsons, Hadley, Mass. and ABI, Baltimore, Md.) weighing 8±3 kg. Heparin (Elkins-Sinn, Cherry Hill, N.J.) was administered intravenously at 0.5 mg/kg and donors anesthetized with a mixture of Telazol (7-10 mg/kg, Fort Dodge Laboratories, Fort Dodge, La.) and Rompun (5 mg/kg, Miles, Inc., Shawnee, Mission, Kans.). Plane of anesthesia was maintained with isoflurane gas. All procedures were performed in compliance with IACUC guidelines.

Cells were isolated using a modification of the Seglen method (Selgen, "Preparation of isolated rate liver cells," in *Methods in Cell Biology,* Prescott et al., eds. Vol. 13, Academic Press, New York, N.Y., 1976). Briefly, the exposed liver was cannulated and perfused in situ with cold Lactated Ringers (Baxter, Deerfield, Ill.) at 20 mllmin before excision. The liver quickly was warmed and perfused with 0.2% EDTA at 37° C. followed by perfusion of 1 mg/mL collagenase (Life Technologies, Grand Island, N.Y.) at 37° C. until digestion appeared complete (typically after 18-26 minutes). Further digestion was stopped with the addition of cold Hank's buffered saline solution (BioWhittaker, Walkerville, Md.) supplemented with 10% HS. Undigested tissue and gall balder were excised and the remainder of the tissue passed sequentially through a stainless steel sieve (Fisher Scientific, Pittsburgh, Pa.) with 200 µm-diameter pores. The suspension of cells then was washed twice and resuspended in base culture medium.

Figure 10:
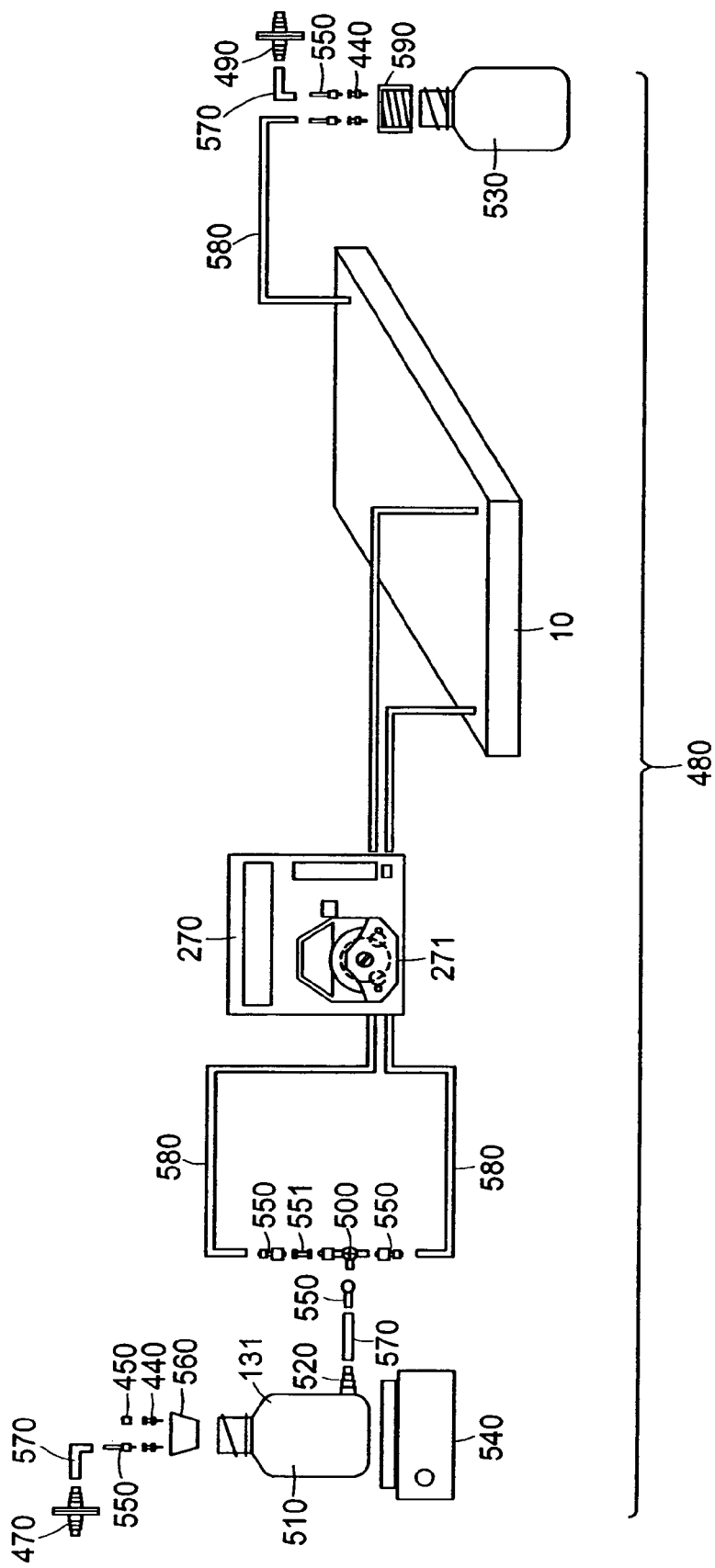
FIG. 10 is a schematic diagram of a closed system for seeding a closed chamber with cells by perfusion from a reservoir.

The cells then were seeded into the chamber 10 using the apparatus 480 depicted in FIG. 10. All steps were conducted aseptically with sterile components within a BSC unless otherwise stated to insure sterility, although conceptually a BSC is not needed if a tubing welder is used to make aseptic connections. However, for simplicity a tubing welder was not used in these studies.

In some studies the gas-permeable, liquid-impermeable film was pre-coated with a sterile 160 mL-volume solution of 44 µg/mL Type I collagen in distilled, deionized water for 30-60 minutes. Using a BSC this solution was introduced into the chamber 10 by removing female Luer-lock plugs from a pair of Luer-lock ports on the outer face of the top of the chamber, dispensing the solution into a now-open port with a 50 mL-volume pipette while venting the gaseous contents of the compartment into the BSC through the other now-open port, and reinstalling the Luer-lock plugs onto their respective fittings. Subsequently, the solution of unadsorbed collagen was removed by again removing the above pair of Luer-lock plugs, aspirating the compartment with a 2 mL-volume Pasteur pipette placed in an open fitting just vacated by a Luer-lock plug, rinsing the compartment with 50 mL of base culture medium by pipette, and aspirating this rinsate as described for the solution of collagen. The result is a coating of molecular thickness of collagen on the film.

Cells were seeded into an individual chamber 10 from a suspension of cells 131 prepared at a concentration of $5 \times 10^6$ cells/mL in a 1 L-volume Pyrex® aspirator bottle 510 with tubulation 520 (Fisher Scientific) with stopper 500, filter 490, and associated parts 440, 450, 550, and 570 for venting during seeding. The flask was placed on a shaker 540 to keep the suspension well mixed and minimize settling of cells during seeding. The chamber was prepared for seeding by removing three Luer-lock plugs from Luer-lock fittings on the outer face of the top of the chamber.

The apparatus 480 for dispensing cells 130 into the chamber 10 then was assembled by connecting the tubulation 520 to a segment of Tygon® LFL US® 17 Masterflex® 0.25"-ID tubing 570 (Cole Parmer Instrument Company, Vernon Hills, Ill.) to barbed-to-male-Luer lock fitting 550 to four-way stopcock 560 to a male Luer lock-to-barbed fitting 550 and female-to-female Luer lock fitting 551 to two parallel segments of Tygon® LFL US® 25 Masterflex® 0.19"-ID tubing 580 (Cole Parmer Instrument Company) to the chamber 10 and from the chamber 10 to a male Luer lock-to-barbed fitting 550 to a segment of Tygon® LFL US® 17 Masterflex® tubing 570 (Cole Parmer Instrument Company) to barbed-to-male Luer lock fitting 840 to an waste receiver 530 formed by an assembly of parts 440, 590, 570, and 490. This receiver 530 allowed aseptic venting of the apparatus 480 to accommodate the gaseous contents displaced from the chamber and tubing during seeding of cells.

Flow in the apparatus 480 was controlled by loading the segments of tubing 580 individually into Easy-Load® pump heads with PSF housing 271 (Cole Parmer Instrument Company) mounted on a L/S® variable-speed digital peristaltic drive with stainless steel rotor 270 (Cole Parmer Instrument Company). The use of dual ports for introducing the suspension of cells 131 facilitated uniform seeding of cells into the chamber 10. Segments of tubing 570 and 580 were selected to match cross-sectional area for flow within segment 570 with the sum of the cross-sectional areas for flow within segments 580. These three segments of tubing were primed with the suspension of cells 131 prior to introduction of cells into the chamber.

To actually seed the suspension of cells 131 into the chamber 10, the chamber was tilted approximately 45° from horizontal on its short axis and filled by pumping 165 mL of the suspension of cells 131 at 50 mi/min through the dual segments of tubing 580. This flow rate was chosen to minimize the time required to seed cells without inducing excessive shear of the suspension. Subsequently, the chamber was tilted back to horizontal, the tubing disconnected from the chamber, and all open ports on the chamber capped. The chamber then was transferred to an incubator operated at 37° C., 10% CO2, and 85% relative humidity. This procedure could be repeated for seeding plurality of chambers.

Example 3

Closed Chamber with Adjustable Volume—Reduction in Volume

The ability of a cell-seeded chamber to be converted from a seeding configuration containing 165 mL of medium to a perfusion configuration containing 35 ML of medium was demonstrated with the chamber 10 of Example 2 depicted in FIG. 9. The chamber was reconfigured after approximately 18-24 hours of static culture by first removing the chamber from the incubator and placing it in a BSC. Next, plugs 450 for ports 116 and 120 were removed, medium in the chamber aspirated through the now-open port 116, the compartment rinsed to remove nonadherent debris by dispensing and aspirating 50 mL of base culture medium through the port 116, and plugs 450 replaced. The volume of the compartment then was reduced by removing plugs for the perfusion fittings 440, loosening the fasteners 70, removing and replacing the four 0.0625"-thick outer shims 60 with a set of four 0.005"-thick polycarbonate shims, and retightening the fasteners 70 as described in Example 2. Shims were removed by pulling out by their tabs. This procedure did not compromise the sterility of the chamber yet decreased the volume of the compartment and associated flow passages four-fold to 35 mL, providing approximately 1 mL for every $2 \times 10^7$ cells seeded.

Perfusate was distributed through the interior of the chamber using internal inlet and outlet manifolds machined into the top plate 30. Perfusate entered through one of the inlet perfusion ports, flowed through the associated 19"-long hole, from which it distributed through the 15 associated cross-holes 390 into the chamber's compartment. The perfusate then flowed through the chamber's compartment, exited through the set of 15 cross-holes 390 into their associated 19"-long hole, and exited the chamber 10 through the perfusion outlet port 100. Flow rates for perfusion were chosen such that flows through the features in the top plate 30 and the chamber's compartment were laminar (i.e., associated Reynolds numbers were less than 2000). The small diameter of the cross-holes 390 relative to the diameter of the 19"-long holes 370 and 380 was selected to uniformly distribute the flow of perfusate through the cross-holes 390 with minimal preferential training of perfusate through a subset of cross-holes, which would result in preferential training of perfusate through the chamber's compartment.

Example 4

Closed Chamber with Adjustable Volume—Perfusion as a Single Cartridge

The ability of a cell-seeded chamber 10 in perfusion configuration to be perfused was evaluated with the chamber of Example 3 and a closed-loop circuit. These tests also permitted study of the function of hepatocytes in vitro under perfusion of medium or plasma, the use of multiple of these chambers manifolded together to treat an animal in liver failure, and confirmation of scaling of per-cell function from these new chambers to chambers previously described in International PCT Application Publication No. WO 00/78932.

A closed-loop circuit for perfusion (i.e., a circuit for perfusion with complete recycle) was assembled with a cell-seeded chamber 10 in its perfusion configuration, a sterile 500 mL-volume receiver with associated cap and fittings, and two segments of 2'-long L/S® 14 Masterflex® 0.06"-ID tubing (Cole Parmer Instrument Company) with associated barbed-to-male Luer lock fittings connecting the chamber and receiver. The receiver was loaded with a defined volume of perfusate prior to hookup. The tubing was Tygori LFL for studies with medium or plasma not containing diazepam; Vitori tubing was used for studies with medium challenged with diazepam. The two segments of tubing connected the inlet and outlet ports of the chamber to the receiver, respectively. Parts were sterilized by steam autoclaving or received sterile prior to assembly.

The assembled circuit for perfusion was transferred from the BSC to an incubator operated at 37° C. and 10% $CO_2$. Tubing connecting the receiver and the inlet port to the chamber was loaded into an Easy-Load® pump head (Cole Partner Instrument Company) mounted on a US® variable-speed digital peristaltic drive with stainless steel rotor (Cole Partner Instrument Company). Next, the medium in the receiver was recirculated through the circuit (i.e., from the receiver through tubing to the chamber through a second set of tubing back to the receiver) at a flow rate typically 10 mUmin. At start-up the chamber 10 typically was tilted from horizontal on its short axis to facilitate removal of air bubbles from the chamber's compartment. The receiver in this circuit also functioned as a bubble trap. After a perfusion for 6, 18, or 24 hours, the recirculating perfusate was sampled and tested for biochemical properties reflective of hepatocyte function, as described in Example 4. Multiple sequential periods of perfusion were possible by exchanging the receiver for a new receiver with fresh perfusate.

Upon completion of a study a chamber 10 was removed from the incubator, disassembled, and cleaned. All tubing and plastic fittings were disconnected and disposed following appropriate procedures for biohazardous materials. Next, the fasteners 70 and stainless steel female Luer-lock fittings for perfusion 440 were removed and cleaned by sonication for 30 minutes. The gas-permeable, liquid-impermeable film was stripped from the film-frame assembly 330, the frame 40 soaked in 70% ethanol in water for 24 hours to loosen residual epoxy, and this epoxy and associated film debris scraped off using a razor blade or scalpel. After removing both the gasket 50 and inner shim 180, the top plate 30 was cleaned by scrubbing with the detergent Bacdown (Decon Labs, Bryn Mawr, Pa.). The 19"-long through holes 370 and 380 were cleaned individually using segments of pipe cleaner and flushing with 1% $H_2O_2$. All parts then were rinsed with water and dried for future use.

Although the described circuit for perfusion had a closed-loop configuration, we anticipate forms of the embodiment described in this Example that have an open-loop configuration in which the flow path is from a supply reservoir, through a pump, through the chamber, and into a collection reservoir. Assembly and operation of this open-loop circuit follows the general procedures described above for a closed-loop circuit.

Example 5

Figure 11:
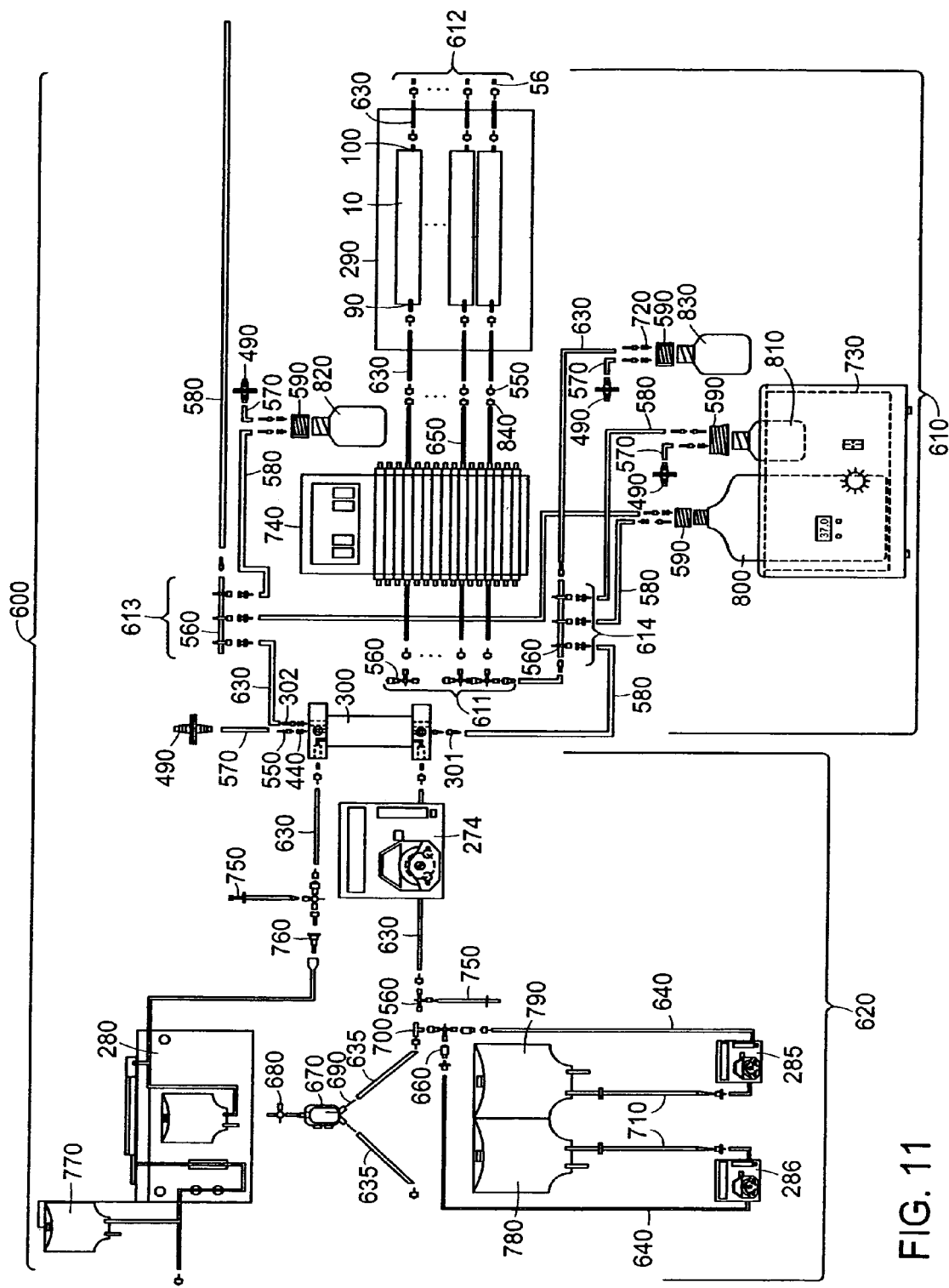
FIG. 11 is a schematic diagram of one embodiment of the extracorporeal system for interfacing a plurality of cell-seeded closed chambers with adjustable volume with a patient in organ failure.
Figure 12A:
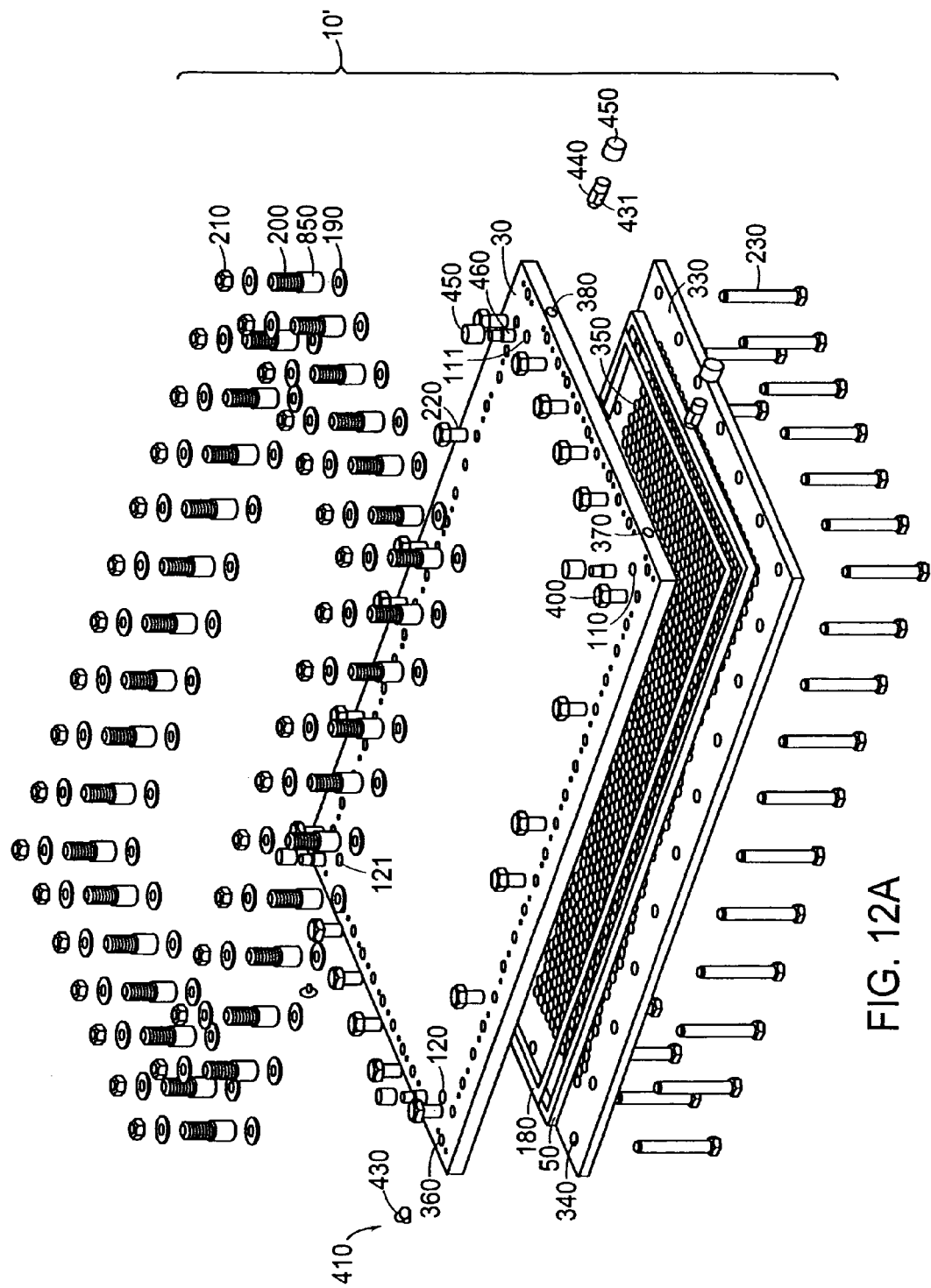
FIGS. 12a, 12b, and 12c are schematic diagrams of perspective views of a closed cell-culturing chamber in which volume is adjusted by removal of distributed and substantially incompressible bolts of fixed length while a minimum stress is applied to the seal using springs.
Figure 12B:
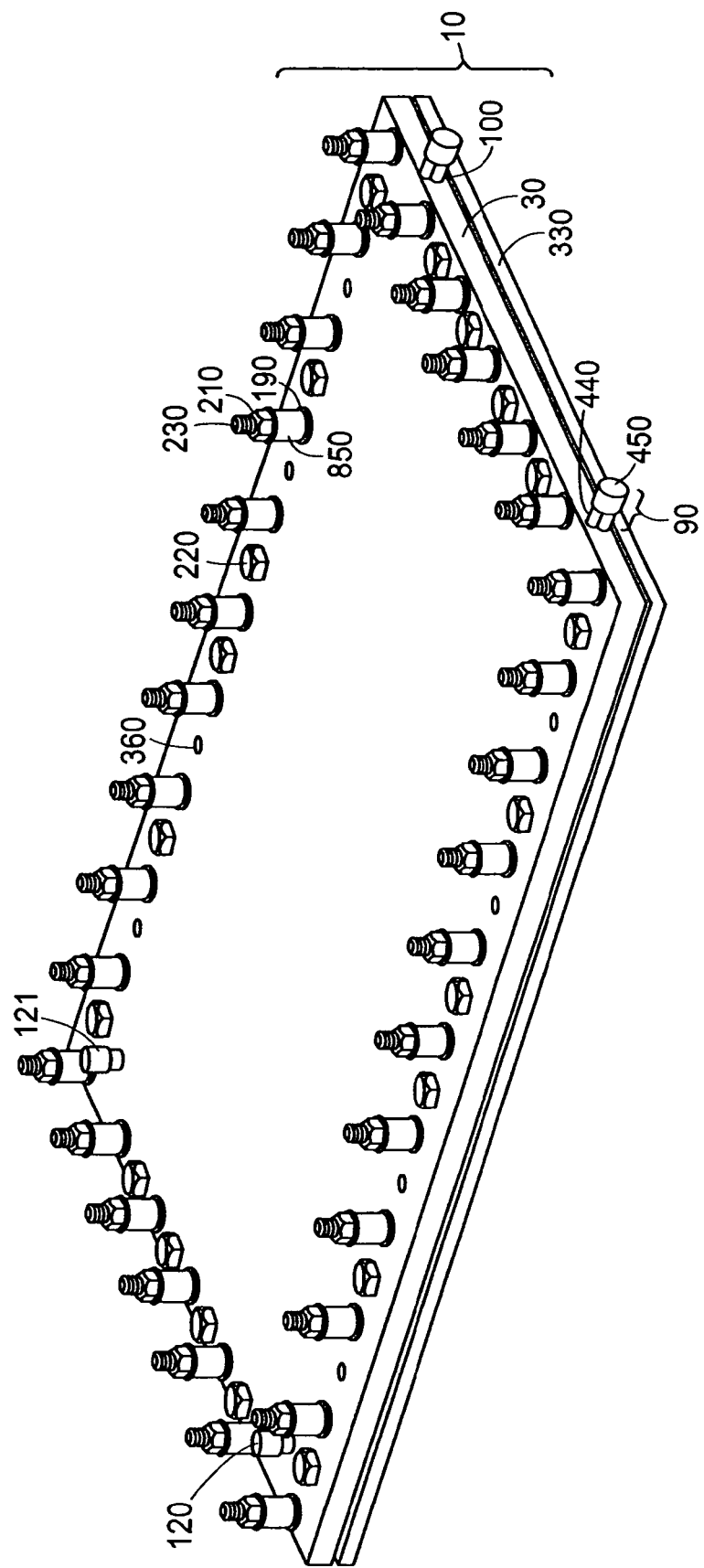
Figure 12C:
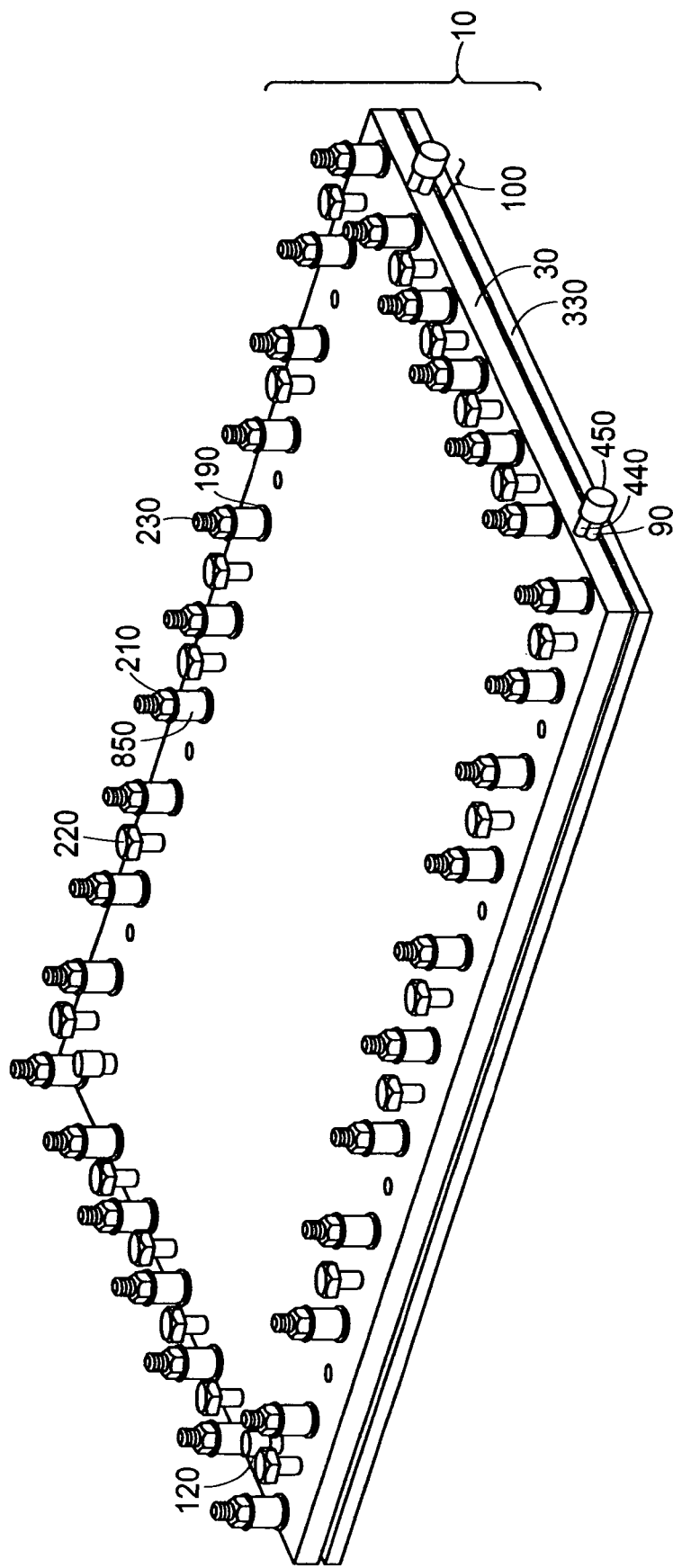

System for Treatment of an Animal in Liver Failure with a System Including a Plurality of Closed Cell-Culturing Chambers with Adjustable Volume Cell-seeded chambers 10 in their perfusion configuration were used as part of an extracorporeal LAD circuit 600 to treat 30-50 lb. pigs in liver failure. This system, as depicted in FIG. 11, consisted of a MCS 9000+ machine 280 (Haemonetics, Inc., Braintree, Mass.) for apheresis, a set of 10 chambers 10 manifolded in parallel, a Model #3110 single-chamber incubator 290 (ThermoForma, Marietta, Ohio) to provide environmental support for these chambers, a water bath 730, and associated pumps, tubing, and other fluid handling accessories. FIG. 11 shows only three chambers for simplicity. The MCS 9000+ is a FDA-approved centrifugally-based device for separating plasma from other blood components. The operation of the MCS is controlled by a user-friendly electronic display requiring minimal operator intervention yet insuring safety of the subject. For example, the MCS automatically controls alternating "Draw" and "Return" cycles for blood flow and responds if limits in the extracorporeal blood volume are reached.

Treatment of a subject with a LAD 600 required multiple phases: a first phase in which hepatocytes were seeded into a plurality of chambers 10 in their seeding configuration (as described in Example 2), a second phase in which the chambers in their seeding configuration were converted to their perfusion configuration (as described in Example 3), a third phase in which the chambers in their perfusion configuration were manifolded in parallel and perfused with base culture medium ("pre-perfusion"), a fourth phase in which the plasma of a pig in liver failure was treated with the extracorporeal LAD, and a fifth phase in which the chambers in their perfusion configuration were re-perfused with base culture medium ("post-perfusion"). Preperfusion provided a baseline for the in vitro performance of the LAD prior to exposure to plasma from a subject with compromised liver function; the ratios of different in vitro hepatocyte functions in post-perfusion to pre-perfusion provided metrics to evaluate how well the cells in the LAD survived exposure to sick plasma.

The extracorporeal LAD 600 with a plurality of chambers 10 consisted of two circuits, the "Device Circuit" 610 and the "Plasma Return Circuit" 620, interfacing through a unit denoted as the "Plasma Reservoir" 300. The Plasma Reservoir was a polycarbonate assembly, based on assemblies described in International PCT Application Publication No. WO 00/78932 as reservoirs, with associated fittings for receipt of plasma from the subject, flow of plasma to and from the Device Circuit through manifolds for medium perfusion 613 and 614, return of plasma back to the subject, and venting the plasma reservoir to prevent build-up of pressure. All parts not previously described in Examples 1, 2, 3, or 4 were sterilized by either gamma irradiation or steam autoclaving. Each segment of tubing described in the following had barbed-to-male Luer lock fittings 550 at each end unless otherwise indicated.

The Device Circuit 610 comprised two sets of device inlet and outlet manifolds 611 and 612, manifolded chambers 10 with associated tubing and fittings leading into and out of the chambers, manifolds for medium perfusion 613 and 614 with associated tubing and fittings, a reservoir for medium for pre- and post-perfusion 800, a reservoir 810 for rinsing cells following treatment of sick plasma, and a waste reservoir 820. Two sets of five cell-seeded chambers in their perfusion configuration, manifolded together in parallel, were assembled as follows. The inlet 90 of each chamber was connected to an inlet manifold 611 for the chambers (formed from one set of four-way stopcocks 560 connected in series) by sequential segments of Watson Marlow Tubing 650 (Watson-Marlow Inc, Wilmington, Del. (with associated fittings 550 and 840 at each end) and of Tygon® LFL US® 14 Masterflex® tubing 630. The outlet port 100 of each chamber was connected to an outlet manifold 612 for the chambers (formed from a second set of four-way stopcocks 560 connected in series) by as second set of segments of Tygon® LFL US® 14 Masterflex® tubing 630.

The remainder of the Device Circuit 610 was formed as follows. The inlet and outlet manifolds 611 and 612 for the two sets of chambers were connected by segments of Tygon® L/S® 25 Masterflex® tubing 580 to inlet and outlet manifolds for medium perfusion 613 and 614, respectively. Each of these latter manifolds comprised 3 four-way stopcocks 560. One stopcock 560 on the inlet manifold for medium perfusion 613 was connected by a segment of Tygon® LFL L/S® 25 Masterflex® tubing 580 to the fitting 301 on the Plasma Reservoir 300, a second stopcock 560 on the inlet manifold for medium perfusion was connected by a segment of Tygon® LFL L/S® 25 Masterflex® tubing 580 to the reservoir inlet for medium perfusion 810, and the third stopcock 560 on the inlet manifold for medium perfusion was connected to the rinse reservoir 810 inlet and the priming reservoir 830 (a disposable 125 mL-volume Nalgene bottle with associated air filter 490) inlet. One stopcock 560 on the outlet manifold for medium perfusion 613 was connected by a segment of Tygon® LFL US® 25 Masterflex® tubing 580 to the fitting 302 on the Plasma Reservoir 300, a second stopcock 560 on the outlet manifold for medium perfusion was connected by a segment of Tygon® LFL US® 25 Masterflex® tubing 580 to the reservoir outlet for medium perfusion 810, and the third stopcock 560 on the outlet manifold for medium perfusion was connected to the waste reservoir 810 outlet. The Device Circuit 610 was pre-perfused for 18 hrs as described in Example 4. Then, the Device Circuit was rinsed with 1 L of base culture medium, during which the contents of the chambers were flushed into the waste reservoir 820. The assembly then was transferred to the operating room for treatment of the pig in liver failure.

The extracorporeal perfusion circuit 600 connected the devices in the subject treatment configuration to the apheresis unit 280. The outlet of the apheresis unit was connected to the Plasma Reservoir 300 aseptically prior to hookup to the subject. The system implemented was based on the use of a 125 mL-volume centrifuge bowl.

Apheresis was started immediately following stabilization of blood pressure after surgery. To minimize hemodilution with healthy plasma, the Plasma Reservoir 300 was primed with medium, with 100 mL of this medium returned to the subject prior to the start of apheresis. Whole blood was drawn by the apheresis unit 280 through the "Draw/Return" line from a cannula implanted in the subject's left femoral artery and separated the blood into plasma and concentrated blood (a mixture of blood cells with a residual amount of plasma). The draw rate was adjustable from 20-80 mL/min. It was desirable to maximize this rate, which was limited by the subject's physiological status, to optimize therapeutic efficacy. The concentrated blood was returned to the subject through the Draw/Return line at 20-60 mL/min. This rate was limited by the diameter of the implanted cannula. A solution of 40 U/mL of heparin in saline was administered by the apheresis unit as anticoagulant at a rate of 1 mL to 15 mL of blood drawn. The plasma was pumped by the apheresis unit into the Plasma Reservoir and sampled from a stopcock on the line from the apheresis unit to the Plasma Reservoir.

From the Plasma Reservoir, plasma was routed through the devices and returned to the subject. Plasma was returned to the subject via the Plasma Return Circuit 620. This circuit consisted of a pump 274, segments of tubing connected to a Radnoti water jacketed bubble trap 670, and a cannula implanted in the subject's left femoral vein. This plasma was supplemented with saline 790 and a solution of 5% dextrose in saline 780, supplied by single-channel digital pumps 285 and 286, respectively. The use of these pumps offered greater control and reliability than infusion of saline and dextrose by IV drip while taking advantage of the vascular access needed for extracorporeal treatment. Saline was infused at a rate of 2 mL/min and dextrose at a rate of 0.30 mL/min-kg body weight (prior to liver failure) and 0.1 mL/min-kg body weight (upon liver failure).

Plasma was treated by perfusion through chambers 10 in the Device Circuit 610 in a recycle loop in which the plasma from the apheresis unit 280 entered the Plasma Reservoir 300 and was circulated through the device manifolds 611 and 612 independent of return to the subject. The Device Circuit interfaced with the Plasma Return Circuit 620 through the Plasma Reservoir. Plasma in this reservoir was recycled continuously through a set of one or more chambers housed in an incubator 290 supplied a mixture of 10% $CO_2$ in air. The volumetric flow rate for perfusion through each individual chamber was 10 mL/min, based on flow rates used to optimize scaling of in vitro function as described in Example 7 below. Plasma was continuously recirculating from the Plasma Reservoir through the Device Circuit by pumping the individual tubings to each chamber at 10 mL/min using a Watson-Marlow 16 channel pump. Plasma was pumped at a variable rate from the Plasma Reservoir using a single-channel digital pump and returned to the subject. The variable rate was determined based on plasma yield per cycle and total cycle time. This method of treatment allowed plasma from each draw cycle to make multiple passes through the Device Circuit before being returned to the subject.

This LAD 600 was run continuously with plasma samples taken every half-hour with syringes located before and after the Plasma Reservoir 300. Following a six hour treatment period from the start of apheresis, the Device Circuit 610 was disconnected from the Plasma Return Circuit 620 by turning the four-way stopcocks 560 in the inlet and outlet manifolds for medium perfusion 613 and 614 to their "f" position. Apheresis was continued for an additional two-hour period and sampling was continued to evaluate effect of treatment with hepatocyte seeded device cartridges. The subject was killed and exsanguinated. The Device Circuit was flushed by changing the position of the stopcocks 560 on the inlet and outlet manifolds for medium perfusion 613 and 614 to allow 1 L of rinse medium to perfuse from the rinse reservoir 810 through the device circuit and into the waste reservoir 820. After the plasma was flushed from the chambers 10, the Device Circuit was perfused with the post-perfusion medium for a period of 18 hours. An 18-hour medium sample was taken, and devices were disassembled and cleaned as detailed in Example 4.

Example 6

Assays for Evaluation of Hepatocyte Function

Hepatocytes have a wide variety of metabolic functions, including anabolism (e.g., synthesis and secretion of glucose and albumin) and catabolism (e.g., metabolism of ammonia and protein catabolic products to urea and detoxification of xenobiotics by conversion from relatively apolar compounds to relatively more polar, conjugated compounds). Catabolism in particular produces compounds that are less toxic and more easily cleared from the body by the renal system (i.e., the kidneys and urine). We evaluated metabolic performance as the rate of ureagenesis (synthesis and secretion of urea), rate of clearance of ammonia, rate of metabolism of the model xenobiotic diazepam, extent of conjugation of metabolites of diazepam, and rate of secretion of glucose into the culture medium. Increases in these properties reflect increased function of the cells. Culture state was determined by the rate of lactogenesis (synthesis and secretion of lactate) and rates of accumulation of the cytosolic enzyme lactate dehydrogenase (LDH), catalyzing the conversion of pyruvate to lactate, and the mitochondrial enzyme aspartate aminotransferase (AST), catalyzing the conversion of the amino group of aspartic acid to a keto group of ketoglutaric acid, in the culture medium. Comparison of these rates among different types of devices allows comparison between the state of cells cultured in these devices.

Ureagenesis was measured for cultures of hepatocytes in devices either perfused for 18 hours with base culture medium or perfused for 24 hrs with base culture medium supplemented with 10 mM exogenous NH4Cl. Samples of 20 µL-volume of hepatocyte-treated medium from individual devices were mixed with 0.5 ml, of 111 g/L of $H_3PO_4$, 3.33 N $H_2SO_4$, 66.7 mg/L $FeCl_3$, 1.67 g/L diacetylmonoxime, and 13.3 mg/L thiosemicarbazone in deionized, distilled water in individual microtubes of a 96-microtube cluster plate (Sigma #07-200-319) prior to incubation at 100° C. for five minutes. Optical absorbance of 200 µL-volume triplicates from each microtube were measured in individual wells of a 96-well plate with a SPECTRAmax® 250 microplate reader (Molecular Devices, Sunnyvale, Calif.). Concentrations then were determined based on the differences in optical absorbance at 540 and 690 nm and a standard curve for 1-100 µg/mL. Rates of ureagenesis were expressed as amount of urea produced per perfused cell seeded per day by multiplying concentrations by volume of perfusate and dividing by the number of cells seeded. In this assay high rates of formation of urea correspond to expected high levels of deamination and clearance of ammonia, clinically desired target functions. The higher the rate of ureagenesis, the greater the expected level of deamination.

The metabolism of diazepam was measured for cultures of hepatocytes in devices perfused for 24 hours with base culture medium supplemented with 25 µg/mL of this drug (D-899; Sigma Chemical, St. Louis, Mo.), solubilized in DMSO at 10 mg/mL, and 1% bovine serum albumin (BSA). Diazepam is the generic name for the benzodiazepine Valium. As a relatively apolar molecule, diazepam is more efficiently cleared by the renal system after two phases of transformation to more polar molecules. Dealkylation and hydroxylation are Phase I processes catalyzed by isozymes of the family of cytochrome P450 mixed-function monooxygenases; for example, the 2C19 isozyme dealkylates diazepam to nordiazepam or temazepam to oxazepam, and the 3A4 isozyme hydroxylates diazepam to temazepam or nordiazepam to oxazepam. Conjugation is a Phase II process mediated by a separate set of enzymes that result in covalent attachment of carbohydrates or sulfates to lipophiles.

Diazepam and its unconjugated and conjugated metabolites were detected and concentrations measured using reverse-phase HPLC. These measurements required the use of tubing in the perfusion circuit made of Viton® which, along with the BSA, minimized nonspecific adsorption of diazepam and metabolites to allow substantially 100% recovery. Samples of hepatocyte-treated medium first were treated with 100 µglucuronidase/sulfatase (S-9751, Sigma) for 3 hours at 37° C. This treatment allowed detection of metabolites glucorinidated or sulfated during Phase IIdetoxification. Next, 400 µL of hepatocyte-treated medium and of glucuronidase-treated, hepatocyte-treated medium were added to 600 µL of methanol in separate 1.5 mL centrifuge tubes, mixed, and spun at 7200×g for 30 minutes at 4° C. Centrifuged samples then were placed in vials of an autosampler to load individual samples onto a C18 column (µBondapak, 3.9×300 mm; Waters Corp., Milford, Mass.). Reverse-phase HPLC was conducted by eluting diazepam and its metabolites in a mobile phase of 60% methanol and 40% 0.03 M potassium phosphate (pH 4.5) at a 1.5 mL/minute flow rate. Elution was measured by optical absorbance at 240 nm with a Coulter Beckman HPLC system (System Gold® model 508 autosampler, model 168 detector, model 126 solvent module). Samples were analyzed with System Gold® 32 Karat™ Software. Standard curves were constructed for diazepam and each metabolite using reference standards (Sigma) prepared in 40% medium and 60% methanol and handled similarly to the samples of cell-treated medium. Standard curves ranged from 2 to 74 µg/mL with lower limits of quantification of 4 µg/mL. Recoveries with the extraction using methanol averaged 82% with coefficients of variations of less than 20%. Overall, this method provided superior recovery compared to existing methods.

Rates of metabolism of diazepam were expressed as total amount of metabolites produced per perfused cell seeded per day by multiplying concentrations by volume of perfusate and dividing by the number of cells seeded. Extents of conjugation were expressed as the ratio of the total concentration of conjugated metabolites to the total concentration of metabolites. In this assay high rates of formation of metabolites reflect high activities for Phase I isozymes, and high extents of conjugation reflect high activities for Phase 11 enzymes.

Lactogenesis was measured using Sigma kit #73510 (St. Louis, Mo.) for cultures of hepatocytes in devices perfused for either 18 or 24 hours with base culture medium. This kit contains a reagent with both an oxidase that converts lactate to pyruvate and $H_2O_2$ and a peroxidase that catalyzes the production of a colorimetric product in the presence of peroxide. Triplicates for 10 µL samples from each device were incubated with 100 µL of kit reagent in individual wells of a 96-well microplate for 10 minutes. Optical absorbance at 540 nm then was measured with a SPECTRAmax® 250 microplate reader. Concentrations were determined based on a standard curve for 0.05-5 mM. Rates of lactogenesis were expressed as amount of lactate produced per perfused cell seeded per day by multiplying concentrations by volume of perfusate and dividing by the number of cells seeded. In this assay similar rates of formation of lactate correspond to cultures with similar physiological states.

Concentrations of LDH and AST in medium from cultures of hepatocytes in devices perfused with base culture medium and of ammonia and glucose from cultures perfused with porcine plasma were measured from 10 µL samples using a Vitroso DT60 II Chemistry System (Ortho-Clinical Diagnostics, Raritan, N.J.). Rates of accumulation of LDH and AST were expressed as amounts of LDH and AST released per perfused cell seeded per day by multiplying concentrations by volume of perfusate and dividing by the number of cells seeded. Similar rates of accumulation of LDH or AST in medium correspond to cultures with similar extents of cell death. Rates of secretion of glucose were expressed as amount of glucose secreted per perfused cell seeded per day by multiplying concentrations by volume of perfusate and dividing by the number of cells seeded. Decreased concentrations of ammonia in plasma and increased concentrations of glucose in medium and plasma (termed "gluconeogenesis") after treatment by hepatocytes reflect increased clinically-relevant functionality of these cells.

Example 7

Comparison of Performance between Previously-Described Cell-Culture Chambers and New Closed Cell-Culture Chamber with Adjustable Volume The performance of hepatocytes perfused in the apparatus of Example 3 was compared to the performance of hepatocytes cultured in two smaller systems described in International PCT Application Publication No. WO 00/78932. In each of these systems, termed henceforth "small," "medium," and "large" devices, hepatocytes were loaded at similar densities onto gaspermeable, liquid-impermeable films of polystyrene (Polyflex), cultured statically for one day with equivalent volumes of medium per cell loaded, and perfused in complete recycle for one day with equivalent volumes of medium per cell loaded and at equivalent shear stresses (calculated based on the height and width of the chamber and the flow rate of perfusate).

The small and medium devices were cell-culture chambers in which cells were seeded by vertically dripping suspensions from a pipette tip onto the culture surface, cultured statically with a removable and loose cover, the medium for seeding cells removed by aspiration after complete removal of the cover, and a cap and tubing subsequently installed to create a closed chamber for perfusion. These operations, with the exception of the static culture, were conducted within a BSC to provide a sterile environment for aseptic processing. In comparison, the large device featured the properties of the invention of the closed chamber with adjustable volume, in particular seeding by perfusion into a closed chamber, aspiration of the medium for seeding cells without compromising the walls of the chamber, and a closed chamber for perfusion created by reducing the volume of the chamber without compromising sterility. Although a tubing welder was not used to make aseptic connections for these studies, only the operations of aspiration and connection of tubing to the closed chamber required the use of a BSC.

The size and operating properties for the small, medium, and large devices consisting of single culture chambers are described in Table 1. The systems for the small and medium devices are approximately $\frac{1}{40}^{th}$ and $\frac{1}{8}^{th}$, respectively, the size of the apparatus of Example 3, although the volumes of the chambers per se during perfusion for the small and medium devices are approximately $\frac{1}{16}^{th}$ and $\frac{1}{12}^{th}$ the volumes of the apparatus of Example 2 and the volumetric flow rate for perfusion differs among the different sizes. However, scaling of performance of cell cultures based on principles for reactor design requires matching the density of cells cultured, the volume of medium perfused per cell, and the mechanical forces experienced (i.e., hydrodynamic shear stresses) among systems of different sizes and not volume of the chamber or flow rate per se. The function and state of a culture depends on the density of cells in the culture, and the depletion and accumulation of compounds in a culture, which in turn affects the function and state of the culture, depend on the volume of medium available per cell. Lastly, the function and state of a culture can be affected by shear stress. Thus, the per-cell rates of ureagenesis, metabolism of diazepam, gluconeogenesis, lactogenesis, and release of LDH and AST should not vary for devices of different sizes seeded at equivalent densities and supplied equivalent volumes of medium per cell. Table 2 shows that such matching was achieved among our systems.

For studies in which cultures were perfused for 24 hours, large devices consisting of single chambers 10 were used, as described in Example 4; for studies in which cultures were perfused for 18 hours, large devices, consisting of 10 individual chambers 10 manifolded in parallel, were used, as described in Example 5.

Table 3 shows that critical hepatocyte-specific properties of ureagenesis and metabolism of diazepam were similar on a per-cell basis among the three different sizes for devices perfused with ammonia- and diazepam-challenged base culture medium for 24 hours. Further, the accumulation of lactate and LDH in the medium was lower, on a per-cell basis, in the closed chamber with adjustable volume 10 than in the smaller devices. It is expected that in vitro ureagenesis correlates with in vivo ureagenesis and deamination, and

TABLE 1

Sizing and Operating Properties of Devices for Perfused Culture of Hepatocytes

| Property | Device Type* | | | Ratio of Property | |
| | Small | Medium | Large | {Large}/{Medium} | {Large}/{Medium} |
| --- | --- | --- | --- | --- | --- |
| Area (cm$^2$) | 23 | 104 | 928 | 8.9 | 40.4 |
| Number of cells cultured | $2.0 \times 10^7$ | $1.0 \times 10^8$ | $8.2 \times 10^8$ | 8.2 | 41.1 |
| Chamber volume (mL) | 2.8 | 2.2 | 35 | 15.9 | 12.5 |
| Perfusate volume for 24-hr studies (mL) | 15 | 75 | 600 | 8.0 | 40.0 |
| Perfusate volume for 18-hr studies (mL) | 10 | 50 | 380 | 7.6 | 38.0 |
| Perfusate flow rate (mL/min) | 1.5 | 0.7 | 10 | 14.3 | 6.7 |

*Sizes based on single chamber per device.

TABLE 2

Scaled Properties of Devices for Perfused Culture of Hepatocytes

| Property | Device Type | | | Ratio of Property | |
| | Small | Medium | Large | {Large}/{Medium} | {Large}/{Medium} |
| --- | --- | --- | --- | --- | --- |
| Cell density (cells/cm$^2$) | $8.7 \times 10^5$ | $9.6 \times 10^5$ | $8.1 \times 10^5$ | 0.84 | 0.93 |
| Perfusate volume per cell for 24-hr studies (nL/cell) | 0.67 | 0.67 | 0.67 | 1.00 | 1.00 |
| Perfusate volume per cell for 18-hr studies (mL/cell) | 0.50 | 0.50 | 0.50 | 1.00 | 1.00 |
| Nominal shear stress in chamber (dynes/cm$^2$) | 1.29 | 1.33 | 1.60 | 1.20 | 1.24 |

Having established operating conditions favorable for scaling among the three differently-sized devices, we evaluated the metabolic performance and culture state of hepatocytes cultured in these devices and compared functions and properties on a per-cell basis. Ureagenesis, metabolism of diazepam, gluconeogenesis, lactogenesis, and release of LDH and AST were determined as described in Example 6.

decreased release of LDH reflects healthier hepatocytes. Decreased lactogenesis in vitro should correlate with decreased acidosis under liver failure. These results support scaling of in vitro function in the new invention, with an improvement in support of some hepatocyte functions compared to cells cultured in apparati requiring additional handling for conversion from seeding to perfusion configuration

TABLE 3

Scaling of In Vitro Hepatocyte Function with Size of Device: Cultures Perfused for 24 Hours

|  | Device Type | | | Ratio of Property | |
| --- | --- | --- | --- | --- | --- |
|  |  |  |  | {Large} | {Large} |
| Property* | Small | Medium | Large | {Medium} | {Medium} |
| Ureagenesis (pg/cell-day) | 50.9 ± 3.7 | 65.3 ± 15.4 | 77.8 ± 9.5 | 1.19 ± −0.32 | 1.53 ± 0.22 |
| Rate of diazepam metabolism (pg/cell-day) | 6.48 ± 0.21 | 4.23 ± 0.66 | 5.11 ± 0.18 | 1.21 ± 0.19 | 0.79 ± 0.04 |
| Extent of diazepam conjugation (%) | 74.4 ± 8.2 | 70.3 ± 37.9 | 79.9 ± 8.6 | 1.14 ± 0.62 | 1.07 ± 0.17 |
| Lactogenesis (pmoles/cell-day) | 0.52 ± 0.04 | 0.56 ± 0.06 | 0.23 ± 0.11 | 0.41 ± 0.20 | 0.44 ± 0.21 |
| LDH released (µU/cell-day) | 0.15 ± 0.01 | 0.16 ± 0.01 | 0.06 ± 0.03 | 0.36 ± 0.20 | 0.42 ± 0.23 |

*Data for ureagenesis, lactogenesis, glucose consumption, and LDH released are averages from three isolations (1137L, 1138L, and 1141L); data for metabolism of diazepam from a single isolation (1141L).

Table 4 shows that ureagenesis was similar on a per-cell basis between the individual small-scale devices referenced above and unchallenged base culture medium for 18 hours and sets of 10 closed chambers 10 in perfusion configuration manifolded together in parallel and perfused as described in Example 5. Further, per-cell rates of lactogenesis and release of the enzymes LDH and AST into the perfusate were similar between the two scales of systems. For these studies we also examined the impact of using a collagen coating, as described in Example 2, on the resulting performance of the systems. No large differences were observed between chambers coated or not coated with collagen. These results further support scaling of in vitro function in the new invention as well as scaling with the number of chambers in the system, supporting the concept of modularity, and the independence of cell function on pre-coating the film 320 with collagen.

Example 8

Treatment of Plasma with Closed Cell-Culturing Chamber with Adjustable Volume

The apparatus of Example 4 was perfused with 100% HS for three hours and the clearance of ammonia and gluconeogenesis examined as described in Example 6. The concentration of ammonia dropped from an initial concentration of 564 µM to an 468±28 µM over the six-hour period, while the concentration of glucose increased from 53 mg/dL to 56±0 mg/dL. These results demonstrate the ability of hepatocytes 130 cultured in closed chambers with adjustable volume to treat plasma of animals.

TABLE 4

Scaling of In Vitro Hepatocyte Function with Size of Device: Cultures Perfused for 18 Hours

|  | Device Type | | | | {Property in Large Device} {Property in Small Device} | |
| --- | --- | --- | --- | --- | --- | --- |
|  |  |  |  |  |  |  |
|  | Small & | Small & Collagen- | Large & | Large & Collagen- |  | Collagen |
| Property* | Uncoated | coated | Uncoated | coated | Uncoated | Coated |
| Ureagenesis (pg/cell-18 hrs) | 19.2 ± 2.9 | 13.5 ± 0.4 | 15.0 ± 5.0 | 18.7 | 0.79 ± −0.12 | 1.38 ± 0.04 |
| Lactogenesis (pmoles/cell-18 hrs) | 0.5 ± 0.1 | 0.5 ± 0.0 | 0.3 ± 0.0 | 0.5 | 0.71 ± 0.13 | 0.95 ± 0.01 |
| LDH released (nU/cell-18 hrs) | <50 | <50 | 55.2 ± 26.4 | 89.2 | >1.11 | >1.78 |
| AST released (nU/cell-18 hrs) | 19.8 ± 5.0 | 36.0 ± 3.0 | 24.5 ± 6.3 | 35.8 | 1.23 ± 0.29 | 0.99 ± 0.09 |

*Data for uncoated culture surfaces from three isolations (1148L, 1149L, and 1150L); data for collagen-coated culture surfaces from a single isolation (1151L).

Example 9

Closed Chamber with Adjustable Volume and Maintenance of Defined Minimum Load on Gasket—Assembly, Seeding with Cells, Reduction in Volume, and Perfusion A modification of the apparatus described in Examples 2 and 3 was developed to decrease handling time during the process to reduce volume and to improve on the design of the chamber using spring-loaded bolts to continuously provide adequate force for gasket compression throughout the reduction in volume process. To set the volume for the seeding configuration, 20 $^5/_{16}$"-18 $^1/_2$"-long 18-8 stainless steel hex head cap screws 220, henceforth denoted as "stand-off bolts" and machined to a defined length were fastened into the top plate 30 to create a compartment 20 0.060"-deep when bottomed out on the film-frame assembly 330 prepared according to Example 1. Two sets of 6¼"-diameter holes 221, 0.825" in from each end along the long axis of the plate, and two sets of 4¼"-diameter holes 221, 0.34" in from the end along the short axis of the plate, were tapped with $^5/_{16}$"-18 threads to enable the fastening of the stand-off bolts 220.

The top plate 30 and film-frame assembly 330 were assembled using $^{32}$¼"-28 1¾"-long 18-8 stainless steel hex head cap screws 230 which, when passed through the plates, were each loaded with a spring 200 (with spring constant 119.7 lbf/in) sandwiched between two ¼" diameter 18-8 stainless steel washers 190 and secured with a nut 210. The amount of force needed to uniformly compress the gasket 50 to ensure a liquid-tight seal was supplied by tightening the nut such that spring height changed from a free height of 0.75" to a compressed height of 0.545". Otherwise, the chamber 10 was assembled and seeded as described in Example 3, with the substitution of the stand-off bolts 220 for the outer shims 60 and the spring-loaded screws 230 for the Southco® fasteners. The stand-off bolts and spring-loaded screws alternated in a pattern which provided the amount of force needed to uniformly compress the gasket as well as the number of stand-off bolts needed to create a uniform volume for the compartment 20 with minimal plate bowing.

To reconfigure the chamber 10 into its perfusion configuration, the cell-seeded chamber with spring-loaded bolts in seeding configuration was connected to the circuit for perfusion described in Example 4. The stand-off bolts 220 were loosened a ¼ turn using a hex head wrench, removing their "stand off" feature from the assembly. As the springs 200 continued to compress the gasket 50, the top plate 30 and film-frame assembly 330 slowly bottomed out on the substantially incompressible 0.005" inner shim 180 previously described in Example 2, reducing the volume of the compartment and causing the fluid inside the chamber to exit through the perfusion inlet and outlet manifolds. The chamber then was perfused as described in Example 4.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A liver assist system comprising:
   a flow-through device comprising a chamber with adjustable volume, the chamber comprising an inlet and an outlet;
   a first conduit for conducting blood plasma from a patient to the inlet;
   a second conduit for conducting treated plasma from the flow-through device to the patient; and
   one or more pumps for moving plasma through the conduits and flow-through device.

2. The liver assist system of claim 1, wherein the chamber with adjustable volume comprises:
   a compartment formed between top and bottom plates separated by a gasket;
   an interior surface on the bottom plate for culturing cells; and
   a means for changing the volume of the compartment by changing the distance between top and bottom plates while the gasket maintains a liquid-tight and sterile seal.

3. The liver assist system of claim 1, wherein the chamber with adjustable volume comprises:
   a compartment formed between top and bottom plates separated by a gasket;
   an interior surface on the bottom plate for culturing cells; and
   a component for changing the volume of the compartment by changing the distance between the top and bottom plates, wherein the component is selected from the group consisting of an incompressible spacer, a spring loaded bolt, a captive fastener, a quarter-turn fastener, and a threaded bolt.

4. The liver assist system of claim 1, further comprising a plasma separator.

5. The liver assist system of claim 1, wherein the chamber further comprises hepatocytes.

6. The liver assist system of claim 1, further comprising a surface for culturing cells, wherein the surface is a gas-permeable, liquid-impermeable film.

7. The liver assist system of claim 6, wherein the gas-permeable, liquid-impermeable film is polystyrene.

8. The liver assist system of claim 6, wherein the gas-permeable, liquid-impermeable film is treated by corona discharge.

9. The liver assist system of claim 6, wherein the gas-permeable, liquid-impermeable film is coated with collagen.

* * * * *